(12) United States Patent
Riahi et al.

(10) Patent No.: US 11,566,885 B2
(45) Date of Patent: *Jan. 31, 2023

(54) METHOD FOR RELATIVE LEAD OFFSET DETERMINATION

(71) Applicant: BIOTRONIK SE & CO. KG, Berlin (DE)

(72) Inventors: Pamela Shamsie Victoria Riahi, Portland, OR (US); Andrew B. Kibler, Lake Oswego, OR (US); Sean Slee, Tigard, OR (US); Christopher S. De Voir, Tigard, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 648 days.

This patent is subject to a terminal disclaimer.

(21) Appl. No.: 16/667,229

(22) Filed: Oct. 29, 2019

(65) Prior Publication Data
US 2020/0132434 A1 Apr. 30, 2020

Related U.S. Application Data

(60) Provisional application No. 62/753,106, filed on Oct. 31, 2018.

(51) Int. Cl.
| | | |
|---|---|---|
| *A61N 1/04* | (2006.01) | |
| *G01B 7/31* | (2006.01) | |
| *A61N 1/36* | (2006.01) | |
| *A61N 1/372* | (2006.01) | |
| *A61N 1/05* | (2006.01) | |
| *A61N 1/08* | (2006.01) | |

(52) U.S. Cl.
CPC ........... *G01B 7/31* (2013.01); *A61N 1/36062* (2017.08); *A61N 1/372* (2013.01); *A61N 1/0551* (2013.01); *A61N 1/36125* (2013.01); *A61N 2001/083* (2013.01)

(58) Field of Classification Search
CPC .............................. A61N 1/371; A61N 1/0551
See application file for complete search history.

(56) References Cited

U.S. PATENT DOCUMENTS

| | | |
|---|---|---|
| 7,684,869 B2 | 3/2010 | Bradley et al. |
| 8,233,992 B2 | 7/2012 | Zhu et al. |
| 8,682,447 B2 | 3/2014 | Bradley et al. |
| 10,928,181 B2 * | 2/2021 | Riahi ........................ G01B 7/31 |

* cited by examiner

*Primary Examiner* — Alyssa M Alter
(74) *Attorney, Agent, or Firm* — Laurence A. Greenberg; Werner H. Stemer; Ralph E. Locher

(57) ABSTRACT

A method for estimating an offset between a first group and a second group of contacts with respect to a longitudinal direction. Each group of contacts includes a plurality of electrodes arranged along a surface of a body of a lead. The method includes the steps of: (a) Selecting a number of electrode pairs, each electrode pair including an electrode of the first contact group and an electrode of the second contact group, and measuring the impedances between the electrodes of each selected electrode pair; (b) pre-conditioning the measured impedances for attenuating unwanted noise to generate pre-conditioned impedances, and (c) determining the lead offset using the pre-conditioned impedances.

13 Claims, 14 Drawing Sheets

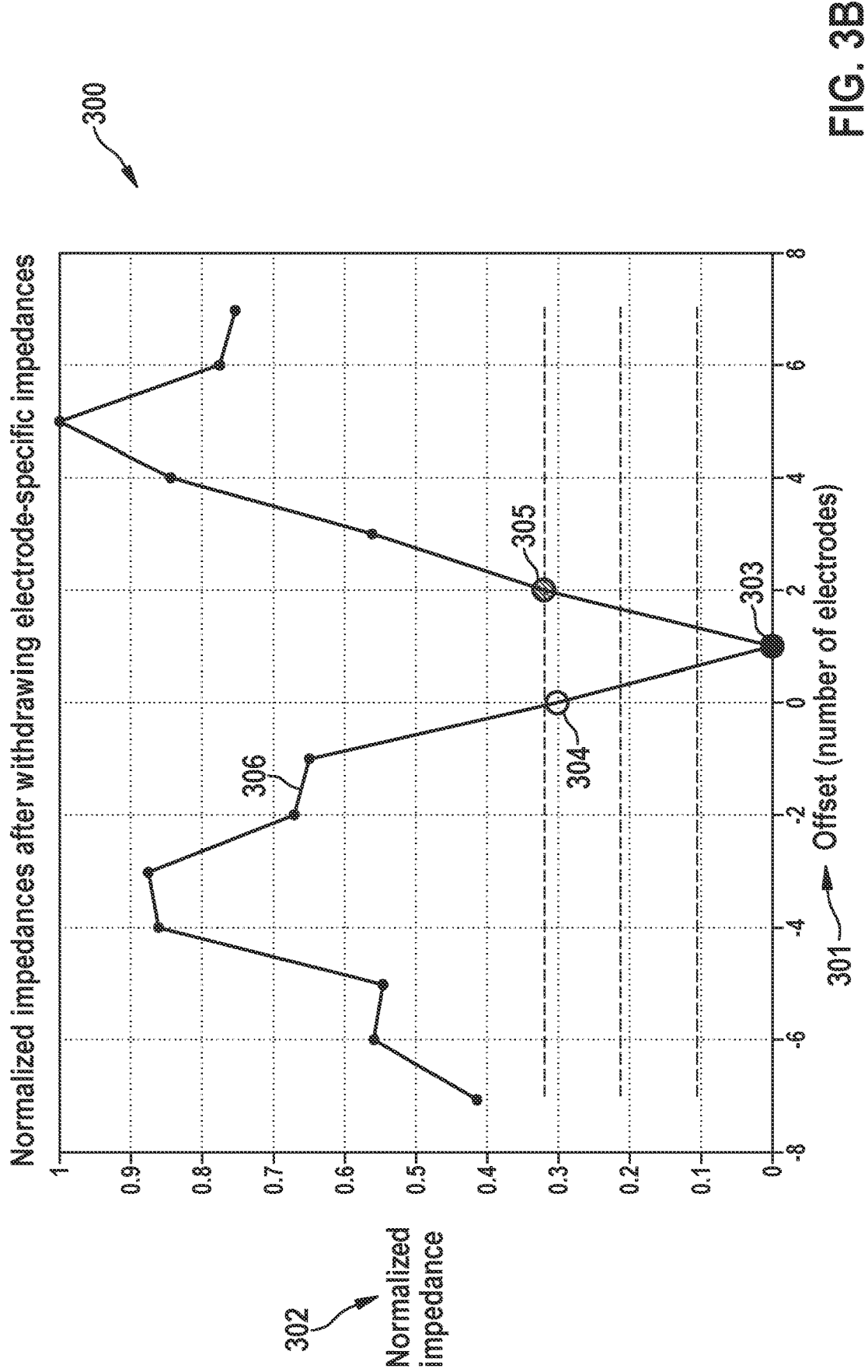

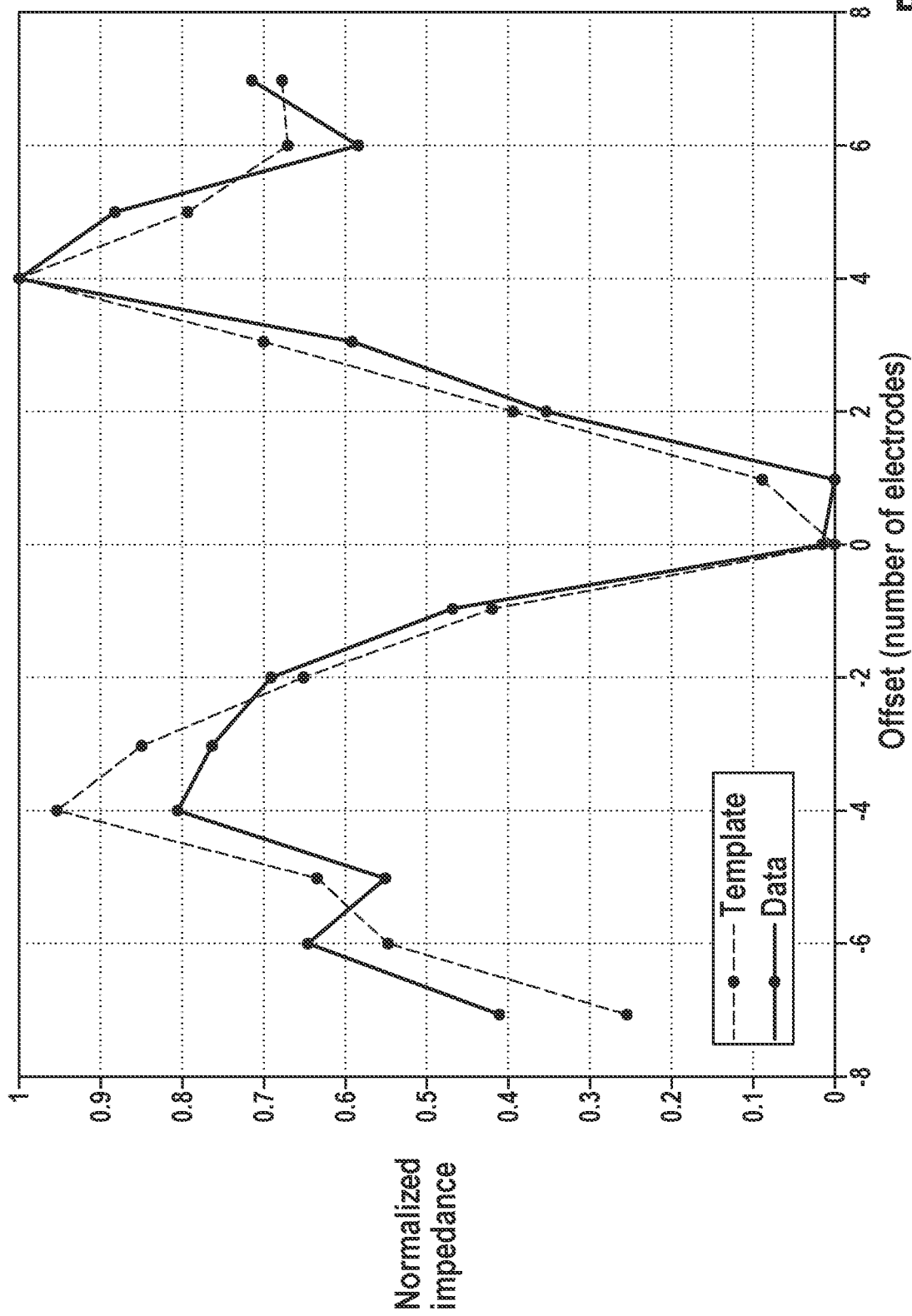

| Electrode # | 1 | 2 | 3 | 4 | 5 | 6 | 7 | 8 |
|---|---|---|---|---|---|---|---|---|
| 9 | | | $Z_{3,9}$ | $Z_{4,9}$ | | | $Z_{7,9}$ | $Z_{8,9}$ |
| 10 | $Z_{1,10}$ | $Z_{2,10}$ | | | $Z_{5,10}$ | $Z_{6,10}$ | | |
| 11 | | | $Z_{3,11}$ | $Z_{4,11}$ | | | $Z_{7,11}$ | $Z_{8,11}$ |
| 12 | $Z_{1,12}$ | $Z_{2,12}$ | | | $Z_{5,12}$ | $Z_{6,12}$ | | |
| 13 | | | $Z_{3,13}$ | $Z_{4,13}$ | | | $Z_{7,13}$ | $Z_{8,13}$ |
| 14 | $Z_{1,14}$ | $Z_{2,14}$ | | | $Z_{5,14}$ | $Z_{6,14}$ | | |
| 15 | | | $Z_{3,15}$ | $Z_{4,15}$ | | | $Z_{7,15}$ | $Z_{8,15}$ |
| 16 | $Z_{1,16}$ | $Z_{2,16}$ | | | $Z_{5,16}$ | $Z_{6,16}$ | | |

FIG. 12

METHOD FOR RELATIVE LEAD OFFSET DETERMINATION

CROSS-REFERENCE TO RELATED APPLICATION

This application claims the benefit, under 35 U.S.C. § 119(e), of provisional patent application No. 62/753,106 filed Oct. 31, 2018; the prior application is herewith incorporated by reference in its entirety.

BACKGROUND OF THE INVENTION

Field of the Invention

The present invention relates to a method and a system for estimating a lead offset between a first lead and a second lead with respect to a longitudinal direction along which the respective lead extends.

In the field of neuromodulation, particularly in the field of implantable neuromodulation devices which comprise multiple electrodes for contacting tissue to apply neurostimulation that are arranged in an array with varying positions between groups of electrodes, it is desirable to identify the relative position of said groups during implanting as well as when the electrode leads are already implanted (or during an operation). A shift in the position of a group of electrodes relative to another group may impact the effects of an ongoing therapy, indicating a need to adjust the therapy's parameters or re-adjust electrode position.

Spinal cord stimulation (SCS) leads are implanted in a specific position and orientation to steer the electrostimulation delivered through one or a combination of multiple electrodes on the electrode leads towards neural elements in the spinal cord that influence nociception and can alleviate chronic pain. The relative position of the electrode leads with respect to each other is a critical factor in SCS therapy efficiency: pain relief can be substantially decreased if the electrode leads shift, which could require electrostimulation reprogramming to compensate for the offset, or surgical intervention to reposition the leads.

Present processes to determine the position of the leads using medical imaging, such as radiography and fluoroscopy, entail significant cost and time, as the patient has to be examined at the hospital.

Furthermore, it is known in the field to use measurements of electric fields of inactive electrodes induced by activation of other electrodes to deduce electrode lead offset with a minimum finding method. Other measurements relate to inter-electrode electric fields and comparison with cross-lead field potential profiles generated by reference models of the appropriate device geometry and configuration built beforehand, via early measurements at implantation, or computational methods. Furthermore, inter-electrode impedance measurements between all opposing electrode leads and deduction of electrode lead offset with a minimum finding method has also been described.

Particularly, U.S. Pat. No. 7,684,869 B2 discloses a method for evaluating electrode lead orientation by calculating monopolar and bipolar impedances between all electrode combinations, calculating corrected impedance values in order to generate an impedance map for the electrode configuration, and determining the electrode combinations with minimum impedance as relatively adjacent electrodes.

Furthermore, U.S. Pat. No. 8,682,447 takes impedance measurements between all inter-lead electrode pairs and may therefore require significant memory capacity and increased battery consumption. The resolution of the method is one electrode (contact), which prevents users from detecting lead shifts less than one electrode/contact and reduces the probability of taking effective corrective actions, such as, appropriate electrostimulation reprogramming to compensate for a specific lead shift based on the detected lead positioning. Furthermore, U.S. Pat. No. 8,682,447 proposes utilizing electric field measurements, and therefore, requires the use of electric currents with sufficient amplitudes to induce measurable electric fields at non-active electrodes, though non-perceptible or perceptible but tolerable by subject, may demand more energy than impedance measurements. In addition, the determination of lead shifts is based on a comparison of the measured electric fields with a previously saved data set, which imposes the additional burden of making a lead measurement at implantation. The solution proposed in U.S. Pat. No. 8,233,992 B2 and others teach the generation of an electrical profile based on a known lead staggered configuration, and using that profile along with modeling to estimate electrode positions from a plurality of other cross-lead measurements. Electrical profiles generated from electrode sources on SCS leads are however easily influenced by localized tissue properties, and there is a likelihood that the reference electrical profile generated from a known staggered lead configuration will not match the measured lead profile due to tissue inhomogeneity. While this does not preclude the calculation of a lead offset estimate, it reduces the accuracy and reliability of said estimate significantly.

Finally, several series of measurements can be required, in order to accurately determine if the leads have shifted which can require variable amounts of memory capacity and may be more energy-consuming.

SUMMARY OF THE INVENTION

Based on the above, it is an object of the present invention to provide for a solution to remotely determine the relative position of the electrode leads with respect to one another while particularly avoiding excessive use of the system's memory and significant reduction of battery life, and particularly without requiring the patient to undergo medical imaging.

This capability could result in better management of the SCS therapy through early detection of electrode lead shifts while preserving battery life.

With the above and other objects in view there is provided, in accordance with the invention, a method for estimating an offset between a first and a second group of contacts with respect to a longitudinal direction or a position of a first group of contacts or second group of contacts with respect to a longitudinal direction, is proposed, wherein each group of contacts comprises a plurality of electrodes arranged along a surface of a body of a lead, the method comprising the steps of:

(a) selecting a number of electrode pairs, each electrode pair comprising an electrode of the first contact group and an electrode of the second contact group, and measuring the Impedances between the electrodes of each selected electrode pair), (b) pre-conditioning the measured impedances for attenuating unwanted noise to generate pre-conditioned impedances, (c) determining said lead offset or position using the pre-conditioned impedances.

According to the present invention, the proposed method is suitable for estimating an offset between a first and a second group of contacts with respect to a longitudinal direction or a position of a first group of contacts with respect to a second group of contacts with respect to a longitudinal direction. Therefore, the term lead offset is used as a substitute for lead position in the present application.

According to an embodiment, the first and the second contact group are electrode contacts of a medical lead.

According to an embodiment, the offset is a positional offset between two medical leads.

According to an embodiment, the present invention is configured to determine the distance between a multi-electrode lead and a nearby medium, as for instance the cerebrospinal fluid (CSF).

According to an embodiment, a method for estimating a lead offset between a first and a second lead with respect to a longitudinal direction, along which the respective lead extends is disclosed, wherein each lead comprises a plurality of electrodes i, j arranged along a surface of a body of the respective lead, and wherein each electrode i of the first lead is aligned with a corresponding electrode j of the second lead with respect to the longitudinal direction when said offset is zero, the method comprising the steps of:

(a) Selecting a number N of electrode pairs (i, j), each electrode pair (i, j) comprising an electrode (i) of the first lead and an electrode (j) of the second lead, and measuring the Impedances $Z_{i,j}$ between the electrodes (i), (j) of each selected electrode pair (i, j), (b) pre-conditioning the measured impedances $Z_{i,j}$ to attenuate unwanted noise (e.g. electrode-tissue interface impedance contributions to the measured impedances) to generate pre-conditioned impedances) by automatically calculating for each electrode (j) of the second lead (200) an average impedance ($\overline{Z}_j$) from the measured impedances of the electrode pairs ((i, j)) comprising the electrode (j) and subtracting the average impedance ($\overline{Z}_j$) from the measured impedances of the electrode pairs ((i, j)) comprising the electrode (j) to obtain processed impedances ($Z_{i,j}'$), and automatically calculating for each electrode (i) of the first lead (100) an average processed impedance ($\overline{Z}_i'$) from said processed impedances ($Z_{i,j}'$) of the electrode pairs ((i, j)) comprising the electrode (i) of the first lead (100) and subtracting the average processed impedance ($\overline{Z}_i'$) from the processed measured impedances of the electrode pairs ((i, j)) comprising the electrode (i) of the first lead (100) to obtain said pre-conditioned impedances ($Z_{i,j}''$), and (c) automatically determining said lead offset using the pre-conditioned impedances ($Z_{i,j}''$).

Particularly, the method according to the present invention is capable of determining relative lead position between two (e.g. spinal cord stimulation (SCS)) leads based on a set of impedance measurements. This is particularly achieved by measurement refinement via an error estimation and subtraction process, and particularly a subsequent application of one of two specific methods described herein, namely peak detection and validation, or pattern correlation estimation.

According to an embodiment of the method according to the invention, selecting a number N of electrode pairs is performed such that the measurement pairs contain a distribution of contact impedance offsets expected to be experienced by the leads.

In a specific example embodiment, the disclosed device/method can determine the relative position in the longitudinal direction of said leads with a resolution of ¼ electrode and accuracy of ½ electrode.

In the context of the invention, "resolution of one electrode" or "unit of one electrode" refers to the distance formed by the length of an electrode in longitudinal direction of the lead, plus the space between two electrodes of the first or second lead in the longitudinal direction. The said distance can alternatively be measured from the center of the width of one electrode to the center to the neighboring electrode in longitudinal direction.

In other words, in order to estimate the relative position of the (e.g. implanted SCS) leads, a series of impedance measurements between inter-lead electrode pairs (i, j) is conducted, wherein particularly the choice of measurements ensures that all electrodes are equally sampled to gather the same amount of information about electrode-specific noise, and that particularly all longitudinal offsets between electrodes of a pair cover the desired range of detectable lead offsets to allow lead offset detection on this range. Further, particularly, pre-conditioning of the measured data set comprises using the distribution of measurements to subtract estimations of electrode-specific characteristics and extract the characteristic profile that depends on (represents) electrode-to-electrode distances. Further, particularly, the relative lead longitudinal offset is estimated based on the pre-conditioned impedance data set.

As will be described in more detail below, the step of estimating the lead offset can be carried out by, e.g., two different embodiments wherein according to a first embodiment an integer lead offset is estimated based on the minimum of the pre-conditioned impedance profile, and a fractional lead offset is estimated as well based on the integer lead offset and relative comparison of adjacent data points. The lead offset is then given by the sum of the integer and the fractional offset.

Alternatively, as will be described in more detail below, the lead offset can be estimated by calculating the correlation coefficient of the pre-conditioned impedance profile with a series of lead offset-specific templates (also denoted as template profiles herein) particularly generated beforehand and, e.g., embedded in the system. The offset of the template associated with the largest correlation coefficient is then assumed to be the representative lead offset. The templates are particularly not patient-specific and can be determined before implantation of the system, using computational simulations of impedance profiles based on a database of clinical impedance measurements.

Particularly, regarding the present invention, implanting leads into a patient is explicitly not a requisite of the method according to the present invention, which aims at estimating lead offset based on measured impedance values, and does particularly not comprise any surgical steps.

According to an embodiment of the method of the present invention, the number N of selected electrode pairs is smaller than the number of all possible electrode pairs formed by an electrode of the first lead and an electrode of the second lead.

Further, according to an embodiment of the method of the present invention, each of the electrodes of the first and the second lead is included in the selected electrode pairs.

Further, according to an embodiment of the method of the present invention, the electrode pairs are selected such that all electrode offsets in the longitudinal direction between an electrode of the first lead and an electrode of the second lead are represented. Preferably, all possible whole-numbered (positive or negative) electrode offsets are represented. As an example: Assuming a first and a second lead, the first lead having 8 electrodes (1 . . . 8), the second lead having 8 electrodes (9 . . . 16). In case the electrodes are aligned such that electrode pairs (1,9), (2,10), (3,11), (4,12), (5,13), (6,14), (7,15) and (8,16) have lead offset 0. Electrode pair (1,16) has an electrode offset of −7, while electrode pair (8,9) has an electrode offset of 7.

Furthermore, according to an embodiment of the method of the present invention each of the leads comprises 8 electrodes. According to a further embodiment, the number N of electrode pairs is N=32. Furthermore, according to an embodiment, each of the electrodes of the first and the second lead is included in four of the thirty-two selected electrode pairs. Furthermore, according to an embodiment the electrode pairs are selected such that all electrode offsets x (with respect to the longitudinal direction) between an electrode of the first lead and an electrode of the second lead are present in the range from −7 to 7. This range is preferably meant in units of the width of one electrode plus the space between two electrodes. Alternatively, the range is meant in units of the width of the center of one electrode to the center of the neighboring electrode. In either case, e.g., for a lead with 3-mm long electrodes separated by 4 mm of insulating material (=inter-electrode space), 1 electrode offset unit would correspond to 7 mm. Alternatively, for a lead with 2-mm long electrodes and 3-mm long inter-electrode spaces 1 electrode offset unit would translate to =5 mm in this way demonstrating the embodiment is independent of electrode width and spacing so long as it is consistent.

Further, according to an embodiment of the method of the present invention, the method is adapted to estimate said lead offset with an accuracy and resolution of less than the width of an electrode plus the space between two electrodes of the first or second lead in the longitudinal direction. The width can alternatively be measured from the center of one electrode to the center to the neighboring electrode in longitudinal direction.

Particularly, according to an embodiment, the two leads are spinal cord stimulation leads configured to apply spinal cord stimulation to a patient.

Furthermore, according to an embodiment, the electrodes of each lead are equidistantly spaced in the longitudinal direction.

Furthermore, according to an embodiment, the electrodes of both leads comprise an identical width in the longitudinal direction.

Furthermore, according to an embodiment, each two neighboring electrodes of the first lead are separated by an electrically isolated section of the body of the first lead. Likewise, particularly, each two neighboring electrodes of the second lead are separated by an electrically isolated section of the body of the second lead.

Further, according to an embodiment of the method of the present invention, the step of determining said lead offset using the pre-conditioned impedances $Z_{i,j}"$, comprises calculating for each considered electrode offset x (with respect to the longitudinal direction) between an electrode of the first lead and an electrode of the second lead (e.g. for x=−7 to 7 in units of electrode offset) an average impedance value corresponding to an average of the pre-conditioned impedance values for the respective electrode offset x.

Further, according to an embodiment of the method of the present invention, the step of determining said lead offset further comprises normalizing said average pre-conditioned impedance values that can be collected in a vector Y normalized to the interval [0,1].

Further, according to an embodiment of the method of the present invention, the step of determining said lead offset further comprises finding a minimum normalized impedance value among said normalized average pre-conditioned impedance values (vector Y), wherein the corresponding electrode offset corresponds to an integer offset, wherein the lead offset to be determined is the sum of said integer offset and a fractional offset.

Further, according to an embodiment of the method of the present invention, determining said fractional offset comprises the further steps of extracting the two normalized impedance values corresponding to the two considered electrode offsets neighboring the minimum impedance values.

According to an embodiment, the differences between the normalized impedance values adjacent to the minimum normalized impedance value (which is 0 since normalization is made in the [0, 1] interval) are compared against each other as follows:

If the smallest value among the two normalized impedance values adjacent to the minimum normalized impedance value is between 0 and ⅓ (included) of the greatest value among the two normalized impedance values adjacent to the minimum normalized impedance value, then it is estimated that the electrode contacts of one lead are facing the centers of the inter-electrode spaces of the other lead, which translates into a fractional offset of ±0.50 electrodes.

If the smallest value among the two normalized impedance values adjacent to the minimum normalized impedance value is between ⅓ (excluded) and ⅔ (included) of the greatest value among the two normalized impedance values adjacent to the minimum normalized impedance value, then it is estimated that the electrodes of one lead are facing the middle between the electrodes and the centers of the inter-electrode spaces of the other lead, which translates into a fractional offset of ±0.25 electrodes.

Finally, if the smallest value among the two normalized impedance values adjacent to the minimum normalized impedance value is between ⅔ (excluded) and the greatest value among the two normalized impedance values adjacent to the minimum normalized impedance value, then it is estimated that the electrodes of one lead are facing the electrodes of the other lead, which translates into a fractional offset of zero electrodes.

The sign of the fractional offset depends on the considered electrode offset of the greatest value among the two normalized impedance values adjacent to the minimum normalized impedance value with respect to the integer offset: if the considered electrode offset of the greatest value among the two normalized impedance values adjacent to the minimum normalized impedance value correspond to an electrode offset greater than the integer offset, then the sign of the fractional offset is negative. Reciprocally, if the considered electrode offset of the greatest value among the two normalized impedance values adjacent to the minimum normalized impedance value correspond to an electrode offset less than the integer offset, then the sign of the fractional offset is positive.

The following paragraph describes an example to illustrate the above definition. If the minimum normalized impedance value $z_1$ correspond to the electrode offset +1, then the normalized impedance value $z_0$ and $z_2$ at electrode offsets 0 and 2, respectively, are collected in a vector M as follows: [$z_0$, $z_1$, $z_2$]. Say that $z_0$ is smaller than $z_2$, then its relative value compared to $z_1$ and $z_2$ determines the fractional offset as follows:

if $0 \leq z_0 \leq z_2$, then the fractional offset is −0.50 electrode;
if $\frac{1}{3}z_2 \leq z_0 < \frac{2}{3}z_2$, then the fractional offset is −0.25 electrode;
if $\frac{2}{3}z_2 \leq z_0 \leq z_2$, then the fractional offset is 0 electrode.

Conversely, if $z_2$ is smaller than $z_0$, then its relative value compared to $z_1$ and $z_0$ determines the fractional offset as follows:
if $0 \leq z_2 \leq \frac{1}{3}z_0$, then the fractional offset is +0.50 electrode;
if $\frac{1}{3}z_2 < z_2 \leq \frac{2}{3}z_0$, then the fractional offset is +0.25 electrode;
if $\frac{2}{3}z_2 < z_2 \leq z_0$, then the fractional offset is 0 electrode.

The lead offset is therefore the sum of the electrode offset of the minimum impedance value $z_1$ (integer offset), +1, and the fractional offset, 0 in the example given in FIG. 3B, which gives a lead offset of +1 electrode.

See FIG. 3B for a graphical example with the corresponding step-by-step deduction of the lead offset to help illustrate the example above.

Note that when the minimum normalized impedance value correspond to a considered electrode offset that is one of the boundary of the range of possible lead offsets (e.g. −7 or 7 electrodes), then the two adjacent values analyzed to calculate the fractional offset are the two normalized impedance values corresponding to the two considered electrode offsets closest to the integer offset (e.g. the normalized impedance values corresponding to considered electrode offsets of −6 and −5 electrodes if the integer offset is −7 in units of electrodes).

Further, according to an alternative embodiment of the method of the present invention, the step of determining said lead offset using the pre-conditioned impedances $Z_{i,j}''$, comprises calculating for each considered electrode offset x (with respect to the longitudinal direction) between an electrode of the first lead and an electrode of the second lead (e.g. for x=−7 to 7 in units of electrodes) an average impedance value corresponding to an average of the pre-conditioned impedance values for the respective electrode offset x, and forming a pre-conditioned impedance profile, wherein said pre-conditioned impedance profile comprises said averages of the pre-conditioned impedance values for the respective electrode offset x, and wherein a plurality of template profiles is provided, wherein each template profile corresponds to a detectable lead offset and comprises impedance values versus lead offset values, wherein particularly the impedance values are taken from in-vivo measurements and/or from one or several computational or in-vitro simulations, and calculating correlation coefficients between the pre-conditioned impedance profile and all of the template profiles, wherein the lead offset is estimated to be the lead offset of the template profile corresponding to the greatest correlation coefficient.

With the above and other objects in view there is also provided, in accordance with the invention, a system for estimating a lead offset between a first and a second lead with respect to a longitudinal direction, along which the respective lead extends. The system comprises:
a first lead and a second lead, particularly extending in parallel along a longitudinal axis, wherein each lead comprises a plurality of electrodes i, j arranged along a surface of a body of the respective lead,
a measuring unit for measuring Impedances $Z_{i,j}$ between the electrodes i, j of a number of selected electrode pairs (i, j), each electrode pair (i, j) comprising an electrode i of the first lead and an electrode j of the second lead,
an analyzing unit configured to pre-condition the measured impedances $Z_{i,j}$ for attenuating unwanted noise (e.g. electrode-tissue interface impedance contributions to the measured impedances) so to generate pre-conditioned impedances $Z_{i,j}''$, wherein the analyzing unit is further configured to
calculate for each electrode j of the second lead an average impedance $Z_j$ from the measured impedances of the electrode pairs (i, j) comprising the electrode j and subtracting the average impedance $Z_j$ from the measured impedances of the electrode pairs (i, j) comprising the electrode j to obtain processed impedances $Z_{i,j}'$, and
calculate for each electrode i of the first lead an average processed impedance $Z_i'$ from said processed impedances $Z_{i,j}'$ of the electrode pairs (i, j) comprising the electrode i of the first lead and subtracting the average processed impedance $Z_i'$ from the processed measured impedances of the electrode pairs (i, j) comprising the electrode i of the first lead to obtain said pre-conditioned impedances $Z_{i,j}''$, and
determine said lead offset using the pre-conditioned impedances $Z_{i,j}''$.

The analyzing unit can be a processing unit on which a suitable algorithm is executed that receives the measured impedances as an input.

Furthermore, the analyzing unit is configured to conduct the steps of the method according to the present invention (e.g. as stated in one of the claims 2 to 11).

Further, according to an embodiment, a system comprised of an implantable device, leads, and an external interface is disclosed. The system is capable of determining relative lead position or a lead offset between two spinal cord stimulation leads based on a set of impedance measurements, and conveying this to a user. This is achieved by
1) measurement refinement via an error estimation and subtraction process,
2) subsequent application of one of two disclosed approaches: peak detection and validation, or pattern correlation estimation
3) conveyance of the lead offset information to an end user via at least one of a variety of user interface means (display, audio, etc).

According to an embodiment, a system is proposed, comprising an implantable pulse generator (IPG), stimulation leads, and an external programmer device which is in communication with the IPG. The IPG is electrically connected to the leads and the leads terminate in a series of electrodes, designed to provide therapeutic stimulation, for example to a patient's spinal cord. The IPG is capable of performing impedance measurements between lead electrodes, and transmitting the measurement information to the external programmer for analysis which is described in the following. The external programmer receives impedance measurement information and performs calculations as described below to determine the relative lead offset of the distal (contact) end of the implanted leads, and communicates the end result to the user. In other embodiments, the IPG may transmit impedance measurements through a server which may process the data and display the end result on a web page to an end user. Preferably, the lead position or impedance measurements are logged such that the trend over time of lead position may be recorded. Furthermore, the lead relative position measurements may be triggered and transmitted from the stimulator using a remote session, and the lead relative offset may then be calculated and displayed to a remote user for assessment of the patient leads and to provide information relevant to stimulation programming and updates.

Other features which are considered as characteristic for the invention are set forth in the appended claims.

Although the invention is illustrated and described herein as embodied in a method for relative lead offset determination, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3B shows examples of step-by-step deduction of the lead offset according to embodiments of the method according to the invention.

FIGS. 4A-4D show examples of lead offset-specific templates superimposed on pre-conditioned subject impedance data sets. The respective lead offsets of the subject data are FIG. 4A: 0 electrode, FIG. 4B: +0.50 electrode, FIG. 4C: +5.50 electrode and FIG. 4D: greater than or equal to +7.00 electrodes.

FIG. 12 illustrates the impedance measurements matrix Z, filled only with the selection of 32 measurements. The dashed rectangle shows the first set of values over which the average should be calculated to achieve substep (i) of step (b) of the method according to an embodiment.

DETAILED DESCRIPTION OF THE INVENTION

Figure 1:
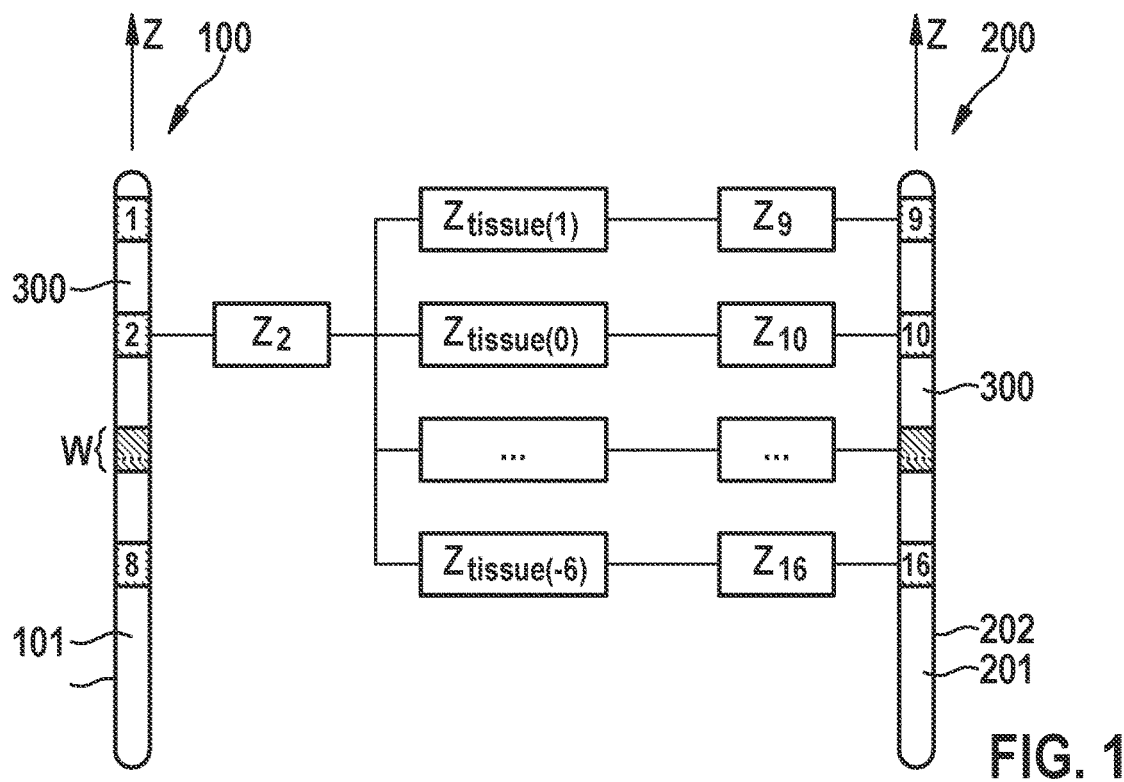
FIG. 1 shows two parallel electrode leads, and the electrical model of impedance measurements. $Z_p$ represents the electrode-tissue interface impedance of electrode p, and $Z_{tissue(q)}$ represents the impedance of the tissue portion that separates two electrodes opposed with a longitudinal offset of q electrodes.

The present invention is particularly based on the concept that inter-electrode impedance measurements can be represented by the electrical model illustrated in FIG. 1, wherein $Z_p$ represents the electrode-tissue interface impedance of electrode p, and $Z_{tissue(q)}$ represents the impedance of the tissue portion that separates two electrodes opposed with a longitudinal offset of q electrodes.

FIG. 1 shows a first and a second lead 100, 200 extending in a longitudinal direction z, respectively, wherein each lead 100, 200 comprises a plurality of electrodes 1, . . . , 8 and 9, . . . , 16, wherein the electrodes 1, . . . , 8 and 9, . . . , 16 are equidistantly spaced along a surface 102, 202 of a body 101, 201 of the respective lead 100, 200 for applying neurostimulation, wherein neighboring electrodes (e.g. 1 and 2 of lead 100) are separated by an electrically isolated section 300 of the body 101, 201 of the respective lead 100, 200.

Each of the electrodes i, j of the respective lead 100 or 200 are electrically connected through respective wires, arranged within the body 101, 201 of the respective lead 100, 200, to an implantable pulse generator (not shown), which is configured to apply electrical stimulation to the patient through selected electrodes via the corresponding wires.

For instance, measuring the impedance between electrode 2 and electrode 10 is equivalent to measuring in series the electrode-tissue interface impedance of electrode 2, the bulk impedance of the tissue that separates electrode 2 and 10, followed by the electrode-tissue interface impedance of electrode 10.

If the leads 100, 200 are aligned, as is the case in the schema of FIG. 1, the portion of tissue separating electrodes 2 and 9 is larger than the portion of tissue separating electrodes 2 and 10, because of the larger distance between the two electrodes 2 and 9. This larger distance is characterized by an offset of one electrode between the two electrodes 2 and 9, as electrode 9 is just one electrode higher than electrode 2 in the longitudinal direction z of the leads 100, 200.

This longitudinal offset between an electrode 1, . . . , 8 of the first lead 100 and an electrode 9, . . . , 16 of the second lead 200 will also be referred to as electrode offset herein and is explicated for each electrode pair formed by an electrode 1, . . . , 8 of the first lead 100 and an electrode 9, . . . , 16 of the second lead 200 in Table 1. Similarly, in the case of non-aligned leads 100, 200, the relative position of the leads 100, 200 is expressed in terms of lead offset, in units of electrodes.

This unit is preferably meant in the width of one electrode plus the space between two electrodes. Alternatively, the range is meant in units of the width of the center of one electrode to the center of the neighboring electrode. In either case, e.g. a lead with 3-mm long electrodes separated by 4 mm of insulating material (=inter-electrode space), that unit would correspond to 7 mm. For a lead with 2-mm long electrodes and 3-mm long inter-electrode spaces, it would translate into an offset of 5 mm.

Assuming a lead offset of +1.00 electrode in FIG. 1 would for instance imply that electrodes 2 and 9 are aligned in FIG. 1.

TABLE 1

Matrix C of electrode offsets corresponding to impedance measurements, assuming lead alignment, in units of electrodes. Electrodes 1 to 8 of first lead 100 are represented by columns 1 to 8 and electrodes 9 to 16 of the opposed second lead 200 by rows 9 to 16.

| Electrode # | 1  | 2  | 3  | 4  | 5  | 6  | 7  | 8 |
|-------------|----|----|----|----|----|----|----|---|
| 9           | 0  | 1  | 2  | 3  | 4  | 5  | 6  | 7 |
| 10          | −1 | 0  | 1  | 2  | 3  | 4  | 5  | 6 |
| 11          | −2 | −1 | 0  | 1  | 2  | 3  | 4  | 5 |
| 12          | −3 | −2 | −1 | 0  | 1  | 2  | 3  | 4 |
| 13          | −4 | −3 | −2 | −1 | 0  | 1  | 2  | 3 |
| 14          | −5 | −4 | −3 | −2 | −1 | 0  | 1  | 2 |
| 15          | −6 | −5 | −4 | −3 | −2 | −1 | 0  | 1 |
| 16          | −7 | −6 | −5 | −4 | −3 | −2 | −1 | 0 |

The contribution of electrode-tissue interface impedance components in measured inter-electrode impedances is significantly greater than tissue-related impedance components, although it is the latter that holds information about leads positions. Particularly, the means according to the present invention attenuates the former factor and extracting the relevant impedance components allowing for lead offset determination.

In the following an embodiment of the method according to the present invention will be explained for two leads 100, 200, wherein each lead comprises 8 electrodes. The method however, also applies to an arbitrary number of electrodes of the leads.

Particularly, according to an embodiment, the method according to the present invention comprises the steps of:
(a) Measure the impedance of a specific selection of 32 electrode pairs between the two opposing leads 100, 200.
(b) Pre-condition the collected 32 impedance measurements data set.
(c) Determine the relative lead longitudinal offset based on the pre-conditioned impedance data set.

Further, according to an embodiment, the third step (c) can be carried out according to two alternative embodiments, namely by means of a method of the minimum impedance value, or by means of the best correlating impedance profile template.

Embodiments and particulars of the three steps (a), (b), and (c) are described in more detail below.

Particularly, measuring the impedance of a specific selection of 32 electrode pairs between the two opposing leads 100, 200 in step (a), as shown on FIG. 1 comprises in an embodiment that the chosen measurements are specifically distributed among all of the 64 possible combinations to allow for
(1) each of the electrodes 1, ... , 8 and 9, ... , 16 to be included in four selected electrode pairs, and
(2) represent all possible longitudinal electrode offsets between an electrode of the first lead 100 and an electrode of the second lead 200.

To illustrate point (1), electrode 1—represented by column 1 in Table 2—is used in four different measurements: it is part of the selected electrode pairs (1, 10), (1, 12), (1, 14) and (1, 16) as indicated in Table 2. By equally distributing the measurements between all electrodes in such a way that each electrode is sampled in the same number of measurements, information about all of the 64 electrode-tissue interface impedances is equally acquired, that is then used to attenuate their weight in the following pre-conditioning step (b).

Further, point (2) refers to the longitudinal offset that can exist between two electrodes of two aligned leads 100, 200, reported for each electrode pair in Table 1. For instance, the offset between the selected pair of electrodes (7,9) and (1,16) is +6 and −7 electrodes, respectively. The 32 selected impedance measurements shown in Table 2 corresponds to offsets of −7 to +7 electrodes (shown in Table 1), which is a preferred requirement to allow for accurate lead offset determination.

TABLE 2

Table showing the distribution of the selected 32 measurements among the possible electrodes combinations. Electrodes 1 to 8 of first lead 100 are represented by columns 1 to 8 and electrodes 9 to 16 of the opposed second lead 200 by rows 9 to 16. $Z_{i,j}$, $i \in \{1, \ldots, 8\}, j \in \{9, \ldots, 16\}$ represents the impedance measured between electrodes i and j.

| Electrode # | 1 | 2 | 3 | 4 | 5 | 6 | 7 | 8 |
|---|---|---|---|---|---|---|---|---|
| 9  |            |            | $Z_{3,9}$  | $Z_{4,9}$  |            |            | $Z_{7,9}$  | $Z_{8,9}$  |
| 10 | $Z_{1,10}$ | $Z_{2,10}$ |            |            | $Z_{5,10}$ | $Z_{6,10}$ |            |            |
| 11 |            |            | $Z_{3,11}$ | $Z_{4,11}$ |            |            | $Z_{7,11}$ | $Z_{8,11}$ |
| 12 | $Z_{1,12}$ | $Z_{2,12}$ |            |            | $Z_{5,12}$ | $Z_{6,12}$ |            |            |
| 13 |            |            | $Z_{3,13}$ | $Z_{4,13}$ |            |            | $Z_{7,13}$ | $Z_{8,13}$ |
| 14 | $Z_{1,14}$ | $Z_{2,14}$ |            |            | $Z_{5,14}$ | $Z_{6,14}$ |            |            |
| 15 |            |            | $Z_{3,15}$ | $Z_{4,15}$ |            |            | $Z_{7,15}$ | $Z_{8,15}$ |
| 16 | $Z_{1,16}$ | $Z_{2,16}$ |            |            | $Z_{5,16}$ | $Z_{6,16}$ |            |            |

Considering that electrode-tissue interface impedances are part of unwanted noise, the pre-conditioning of the collected impedance data set aims at significantly increasing the signal-to-noise ratio by attenuating the electrode-specific impedance component $Z_{i,j}$ from the measured values ($Z_{i,j}$, $i \in \{1, \ldots, 8\}, j \in \{9, \ldots, 16\}$) by sequentially subtracting the average impedance of each electrode, so that an approximation of only the electrode offset-dependent components $Z_{tissue(q)}$, $q \in \{-7, \ldots, 7\}$, remain and can be exploited to determine the lead offset.

According to an embodiment, this pre-conditioning of data particularly comprises the steps described in the following:
(i) Calculate the average $\overline{Z_9}$ of the values in the dashed rectangle of Table 3, omitting the empty cells.

FIG. 12 shows impedance measurements matrix Z, filled only with the selection of 32 measurements. The dashed rectangle shows the first set of values over which the average should be calculated to achieve substep (i) of step (b) of the method according to an embodiment.

(ii) subtract this average $\overline{Z_9}$ from each value of the dashed rectangle, ignoring empty cells, as shown in Table 4.

TABLE 4

Impedance measurements matrix Z for achieving substep (ii) of step (b) of the method according to the present invention.

| Electrode # | 1 | 2 | 3 | 4 | 5 | 6 | 7 | 8 |
|---|---|---|---|---|---|---|---|---|
| 9 |  |  | $Z_{3,9} - \overline{Z_9}$ | $Z_{4,9} - \overline{Z_9}$ |  |  | $Z_{7,9} - \overline{Z_9}$ | $Z_{8,9} - \overline{Z_9}$ |
| 10 | $Z_{1,10}$ | $Z_{2,10}$ |  |  | $Z_{5,10}$ | $Z_{6,10}$ |  |  |
| 11 |  |  | $Z_{3,11}$ | $Z_{4,11}$ |  |  | $Z_{7,11}$ | $Z_{8,11}$ |
| 12 | $Z_{1,12}$ | $Z_{2,12}$ |  |  | $Z_{5,12}$ | $Z_{6,12}$ |  |  |
| 13 |  |  | $Z_{3,13}$ | $Z_{4,13}$ |  |  | $Z_{7,13}$ | $Z_{8,13}$ |
| 14 | $Z_{1,14}$ | $Z_{2,14}$ |  |  | $Z_{5,14}$ | $Z_{6,14}$ |  |  |
| 15 |  |  | $Z_{3,15}$ | $Z_{4,15}$ |  |  | $Z_{7,15}$ | $Z_{8,15}$ |
| 16 | $Z_{1,16}$ | $Z_{2,16}$ |  |  | $Z_{5,16}$ | $Z_{6,16}$ |  |  |

(iii) repeat substeps (i) and (ii) for each row of Table 3, i.e. for electrodes 9 to 16. The result is a new matrix Z' presented in Table 5.

TABLE 5

Impedance measurements matrix Z' after executing substep (iii) of step (b) of the method.

| Electrode # | 1 | 2 | 3 | 4 | 5 | 6 | 7 | 8 |
|---|---|---|---|---|---|---|---|---|
| 9 |  |  | $Z_{3,9} - \overline{Z_9}$ | $Z_{4,9} - \overline{Z_9}$ |  |  | $Z_{7,9} - \overline{Z_9}$ | $Z_{8,9} - \overline{Z_9}$ |
| 10 | $Z_{1,10} - \overline{Z_{10}}$ | $Z_{2,10} - \overline{Z_{10}}$ |  |  | $Z_{5,10} - \overline{Z_{10}}$ | $Z_{6,10} - \overline{Z_{10}}$ |  |  |
| 11 |  |  | $Z_{3,11} - \overline{Z_{11}}$ | $Z_{4,11} - \overline{Z_{11}}$ |  |  | $Z_{7,11} - \overline{Z_{11}}$ | $Z_{8,11} - \overline{Z_{11}}$ |
| 12 | $Z_{1,12} - \overline{Z_{12}}$ | $Z_{2,12} - \overline{Z_{12}}$ |  |  | $Z_{5,12} - \overline{Z_{12}}$ | $Z_{6,12} - \overline{Z_{12}}$ |  |  |
| 13 |  |  | $Z_{3,13} - \overline{Z_{13}}$ | $Z_{4,13} - \overline{Z_{13}}$ |  |  | $Z_{7,13} - \overline{Z_{13}}$ | $Z_{8,13} - \overline{Z_{13}}$ |
| 14 | $Z_{1,14} - \overline{Z_{14}}$ | $Z_{2,14} - \overline{Z_{14}}$ |  |  | $Z_{5,14} - \overline{Z_{14}}$ | $Z_{6,14} - \overline{Z_{14}}$ |  |  |
| 15 |  |  | $Z_{3,15} - \overline{Z_{15}}$ | $Z_{4,15} - \overline{Z_{15}}$ |  |  | $Z_{7,15} - \overline{Z_{15}}$ | $Z_{8,15} - \overline{Z_{15}}$ |
| 16 | $Z_{1,16} - \overline{Z_{16}}$ | $Z_{2,16} - \overline{Z_{16}}$ |  |  | $Z_{5,16} - \overline{Z_{16}}$ | $Z_{6,16} - \overline{Z_{16}}$ |  |  |

(iv) starting with Z', repeat substeps (i) through (iii) of step (b) of the method but for each column of Table 5. The resulting matrix Z" is presented in Table 6.

The impedance matrix Z" in Table 6 represents the pre-conditioned impedance data with attenuated electrode-tissue interface impedance components. The remaining impedances are driven by tissue-related impedance components that are dependent on the distance between electrodes of opposed leads and can therefore be analyzed to determine the relative position of the leads.

TABLE 6 resulting matrix Z"

| Electrode # | 1 | 2 | 3 | 4 | 5 | 6 | 7 | 8 |
|---|---|---|---|---|---|---|---|---|
| 9 |  |  | $Z_{3,9} - \overline{Z_9} - \overline{Z'_3}$ | $Z_{4,9} - \overline{Z_9} - \overline{Z'_4}$ |  |  | $Z_{7,9} - \overline{Z_9} - \overline{Z'_7}$ | $Z_{8,9} - \overline{Z_9} - \overline{Z'_8}$ |
| 10 | $Z_{1,10} - \overline{Z_{10}} - \overline{Z'_1}$ | $Z_{2,10} - \overline{Z_{10}} - \overline{Z'_2}$ |  |  | $Z_{5,10} - \overline{Z_{10}} - \overline{Z'_5}$ | $Z_{6,10} - \overline{Z_{10}} - \overline{Z'_6}$ |  |  |
| 11 |  |  | $Z_{3,11} - \overline{Z_{11}} - \overline{Z'_3}$ | $Z_{4,11} - \overline{Z_{11}} - \overline{Z'_4}$ |  |  | $Z_{7,11} - \overline{Z_{11}} - \overline{Z'_7}$ | $Z_{8,11} - \overline{Z_{11}} - \overline{Z'_8}$ |
| 12 | $Z_{1,12} - \overline{Z_{12}} - \overline{Z'_1}$ | $Z_{2,12} - \overline{Z_{12}} - \overline{Z'_2}$ |  |  | $Z_{5,12} - \overline{Z_{12}} - \overline{Z'_5}$ | $Z_{6,12} - \overline{Z_{12}} - \overline{Z'_6}$ |  |  |
| 13 |  |  | $Z_{3,13} - \overline{Z_{13}} - \overline{Z'_3}$ | $Z_{4,13} - \overline{Z_{13}} - \overline{Z'_4}$ |  |  | $Z_{7,13} - \overline{Z_{13}} - \overline{Z'_7}$ | $Z_{8,13} - \overline{Z_{13}} - \overline{Z'_8}$ |
| 14 | $Z_{1,14} - \overline{Z_{14}} - \overline{Z'_1}$ | $Z_{2,14} - \overline{Z_{14}} - \overline{Z'_2}$ |  |  | $Z_{5,14} - \overline{Z_{14}} - \overline{Z'_5}$ | $Z_{6,14} - \overline{Z_{14}} - \overline{Z'_6}$ |  |  |

TABLE 6-continued resulting matrix Z''

| Electrode # | 1 | 2 | 3 | 4 | 5 | 6 | 7 | 8 |
|---|---|---|---|---|---|---|---|---|
| 15 |  |  | $\frac{Z_{3,15} - Z_{15} -}{Z'_3}$ | $\frac{Z_{4,15} - Z_{15} -}{Z'_4}$ |  |  | $\frac{Z_{7,15} - Z_{15} -}{Z'_7}$ | $\frac{Z_{8,15} - Z_{15} -}{Z'_8}$ |
| 16 | $\frac{Z_{1,16} - Z_{16} -}{Z'_1}$ | $\frac{Z_{2,16} - Z_{16} -}{Z'_2}$ |  |  | $\frac{Z_{5,16} - Z_{16} -}{Z'_5}$ | $\frac{Z_{6,16} - Z_{16} -}{Z'_6}$ |  |  |

Furthermore, according to an embodiment of the method according the present invention, step (c) of the method comprises determining the lead offset between the leads 100, 200 based on the pre-conditioned set of the specifically-selected 32 impedance measurements.

Particularly, two embodiments for achieving this task are explained in the following.

According to a first embodiment a minimum impedance value method can be used to estimate the lead offset.

Figure 2:
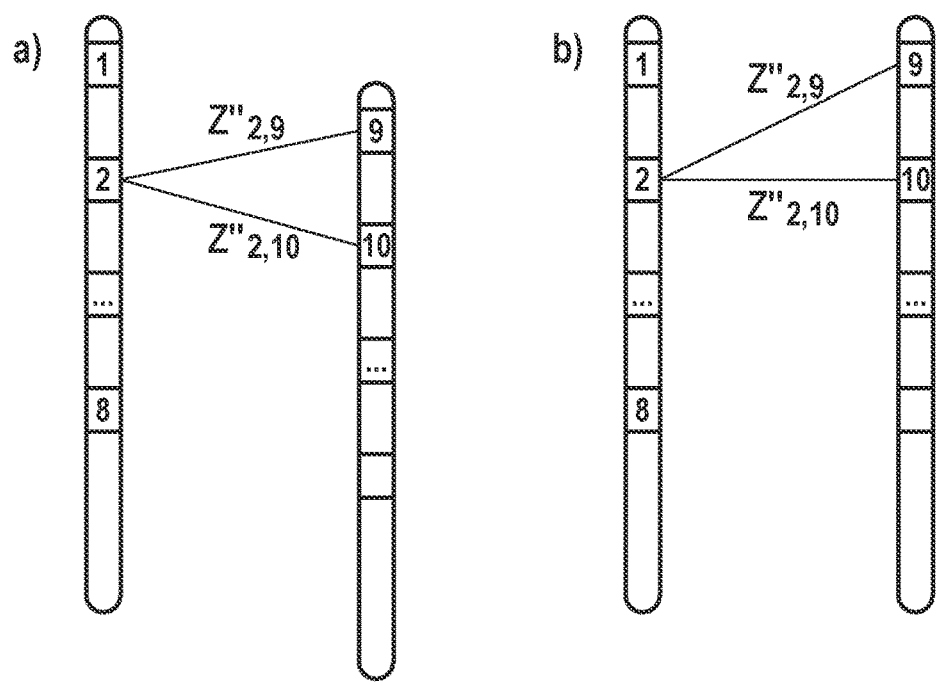
FIG. 2 shows the situation of (a) a non-integer offset where $Z''_{2,9}$ and $Z''_{2,10}$ are theoretically equal and (b) an integer offset where $Z''_{2,9}$ and $Z''_{2,10}$ are theoretically not equal.

This embodiment is based on the postulate supported by subject observation that if the leads 100, 200 have a non-integer relative offset (e.g. every electrode 1, . . . , 8 of a lead 100 is facing an electrically isolated section 300 of the body of the other lead 200), then the impedance measured between this electrode (e.g. 2) and the two electrodes (e.g. 9 and 10) of the opposite lead 200 that are arranged on both sides of the adjacent section 300 are similar, as indicated in FIG. 2(A). On the other hand, in case of an integer offset as shown in FIG. 2(B), $Z''_{2,9}$ and $Z''_{2,10}$ are theoretically not equal.

According to an embodiment, a non-integer offset can be as small as ¼ electrode offset.

Particularly, according an embodiment, the following steps can be conducted to determine the lead offset:

For each electrode offset x from −7 to 7 [electrodes], calculate the average of impedance values measured from electrode pairs that have an electrode offset of x (see Table 1) and are pre-conditioned as described above, wherein the corresponding values are mathematically expressed in Table 6 above. These average values are stored in a vector Y.

Normalize the data in Y to the interval [0, 1].

Find the minimum impedance value of vector Y and its corresponding electrode offset in Table 1: the latter is the integer offset (the lead offset being the sum of the integer offset and a fractional offset determined below), Find the impedance values in Y and their corresponding electrode offsets in Table 1 that are adjacent to the minimum (if the minimum is located on an extremity of the electrode offset range, take the impedance values of the two closest electrode offsets), and store them sequentially in a vector M=[left adjacent value, minimum value, right adjacent value]. Alternatively, vector M can be described as M=[value corresponding to electrode offset Compute the first and second difference of the vector M.

Figure 3A:
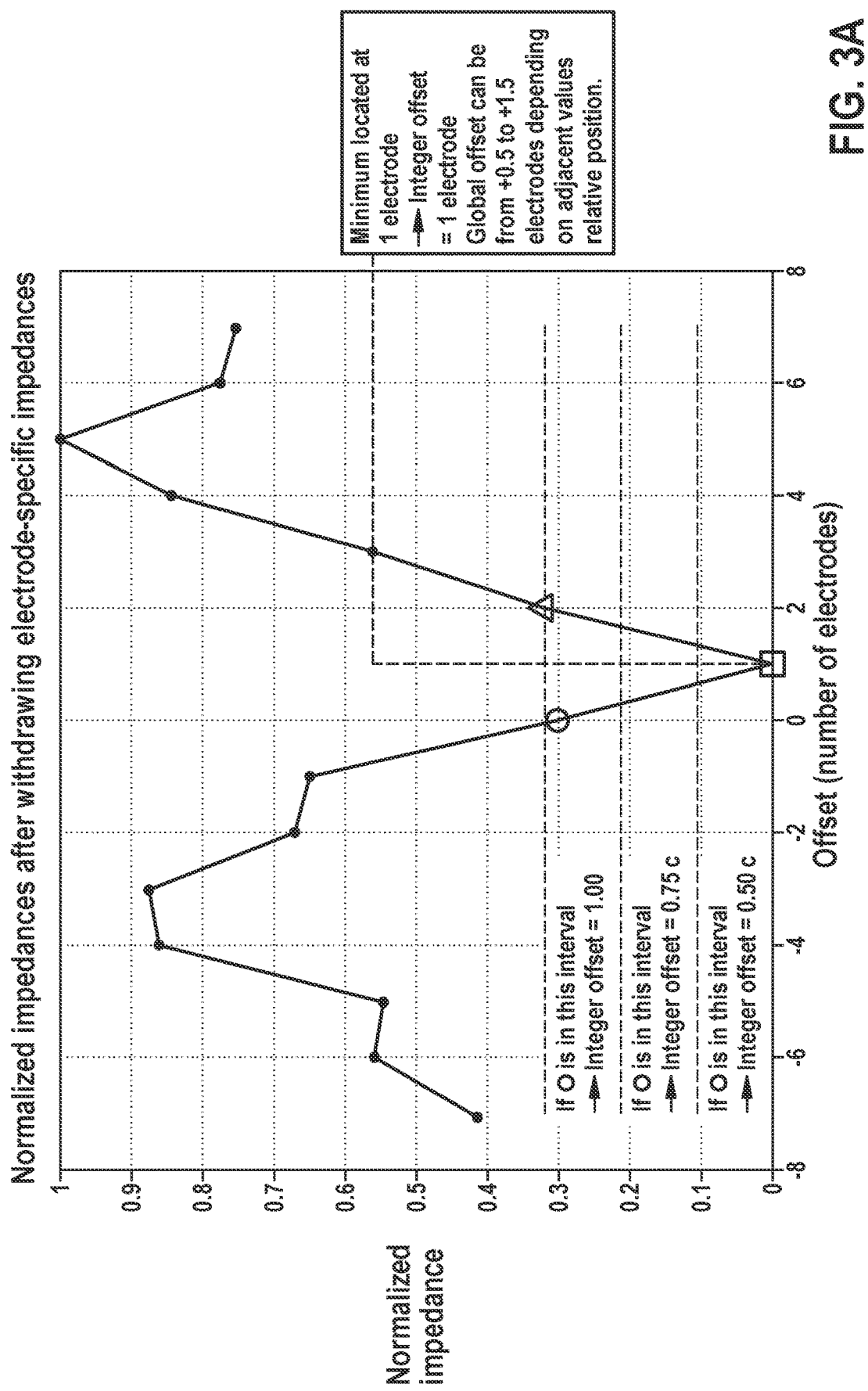
FIG. 3A shows an illustration of lead offset determination using an example of a normalized impedance profile after the pre-conditioning of the data. In this example, the two leads have an offset of +1.00 electrode.

While the integer offset is indicated by the abscissa of the square in FIG. 3A (+1.00 electrode), the fractional offset is determined by the relative value of the minimum between the two data points adjacent to the square (represented by the circle in FIG. 3A) with respect to the maximum between the two data points adjacent to the square (represented by the triangle in FIG. 3A). The calculated fractional offset can be 0, ±0.25 or ±0.50 electrode, with a negative sign if the circle (smaller value) is on the left, and a positive sign if it is on the right. The total lead offset to determine is the sum of the integer and fractional offset.

In other words, the comparison of the first and second difference of vector M determines the fractional offset: if the absolute value of the second difference is inferior to ⅓ of the maximum of the first differential (i.e. if the circle is in the upper interval in FIG. 3A), then the fractional offset is 0 electrode. If it is between ⅓ and ⅔ of the maximum of the first differential (i.e. the circle is in the middle interval in FIG. 3A), then the factional offset is ±0.25 electrode. If it is between ⅔ and ⅓ (i.e. the circle is in the lower interval in FIG. 3A), then the 'fractional' offset is ±0.50. The sign of the fractional offset is determined by the relative position of the second minimum value among the two data points adjacent to the minimum value: the sign is negative if the second minimum corresponds to an electrode offset smaller than the integer offset (e.g. circle in FIG. 3A), and positive if it corresponds to an electrode offset greater than the integer offset.

FIG. 3B shows examples of step-by-step deduction of the lead offset according to embodiments of the method according to the invention. Depicted is a diagram 300 with Contact offset −8 to 8 along x-axis 301, and normalized impedance along y-axis 302. Graph 306 shows the normalized impedances after withdrawing electrode-specific impedances according to aspects of the inventive method. According to the example, the point of minimum impedance 303 is measured at contact lead offset=positive whole-number offset of +1.00. According to an embodiment of the invention, the lead offset can be in this case estimated from +0.50 to +1.50 contacts depending on the adjacent values' relative position. Point 304 corresponds to the minimum impedance among the two points 304 and 305 adjacent to 303. Point 304 is between ⅔ and ⅓ of the maximum adjacent impedance value (point 305). Therefore, in this case the fractional offset equals 0 according to embodiments of the invention, resulting in that the overall lead offset equals +1.00 (positive whole-number offset) minus 0 (fractional offset)=+1.00 unit of electrodes.

According to an alternative embodiment, a method of the best correlating impedance profile template is employed to extract the overall lead offset.

This embodiment is based on the best correlation of the pre-conditioned impedance profile, i.e. the graph representing impedance versus electrode offset after pre-conditioning using the technique described above (cf. Table 6), with a lead offset-specific template (also denoted as template profile).

For each possible lead offset, the corresponding template profile can be generated by averaging a large number of impedance data sets collected from SCS leads used in-vivo or in-vitro or computationally simulated impedance data sets if experimental data is lacking or insufficient. The number of templates to generate depends on the maximum range of detectable lead offsets (−7 to 7 [electrodes] for 8-electrode leads) and on the measurement resolution (i.e. the smallest difference between two different lead offsets), which is 0.25 electrodes in this specific embodiment.

Particularly, this embodiment comprises the steps of:
i. calculating the correlation coefficient between the pre-conditioned impedance profile and all of the lead offset-specific templates (template profiles), and
ii. noting the lead offset of the template profile corresponding to the greatest correlation coefficient.

Alternately, this embodiment, comprises the steps of:
i. calculating the correlation coefficient between the pre-conditioned impedance profile and a set of representative lead offset-specific templates that do not correspond to all potential lead offsets (template profiles)
ii. additionally calculating the correlation coefficient between the pre-conditioned impedance profile and mathematical modifications to lead offset-specific templates which represent a set of templates corresponding to offsets at a finer resolution than the stored set of lead offset-specific templates, and
iii. noting the lead offset of the template profile corresponding to the greatest correlation coefficient.

Particularly, the template profiles are generated via extensive computational simulations at each positive lead offset that can be detected (e.g. from 0 to +7 electrodes with a step of 0.25 electrodes) and are mirrored to generate the negative portion of possible lead offsets (e.g. from −7 to 0 electrodes with a step of 0.25 electrodes) and thus save memory use. The number of templates to be generated is therefore particularly dependent on the resolution: it is equal to the difference between the maximum and minimum of the detectable positive lead offset range divided by the resolution, plus one (e.g., 29 templates for a positive range of 0 to 7 electrodes and a resolution of 0.25 electrodes). The templates are generated beforehand and they can be stored in a device ROM saving working memory.

Figure 4A:
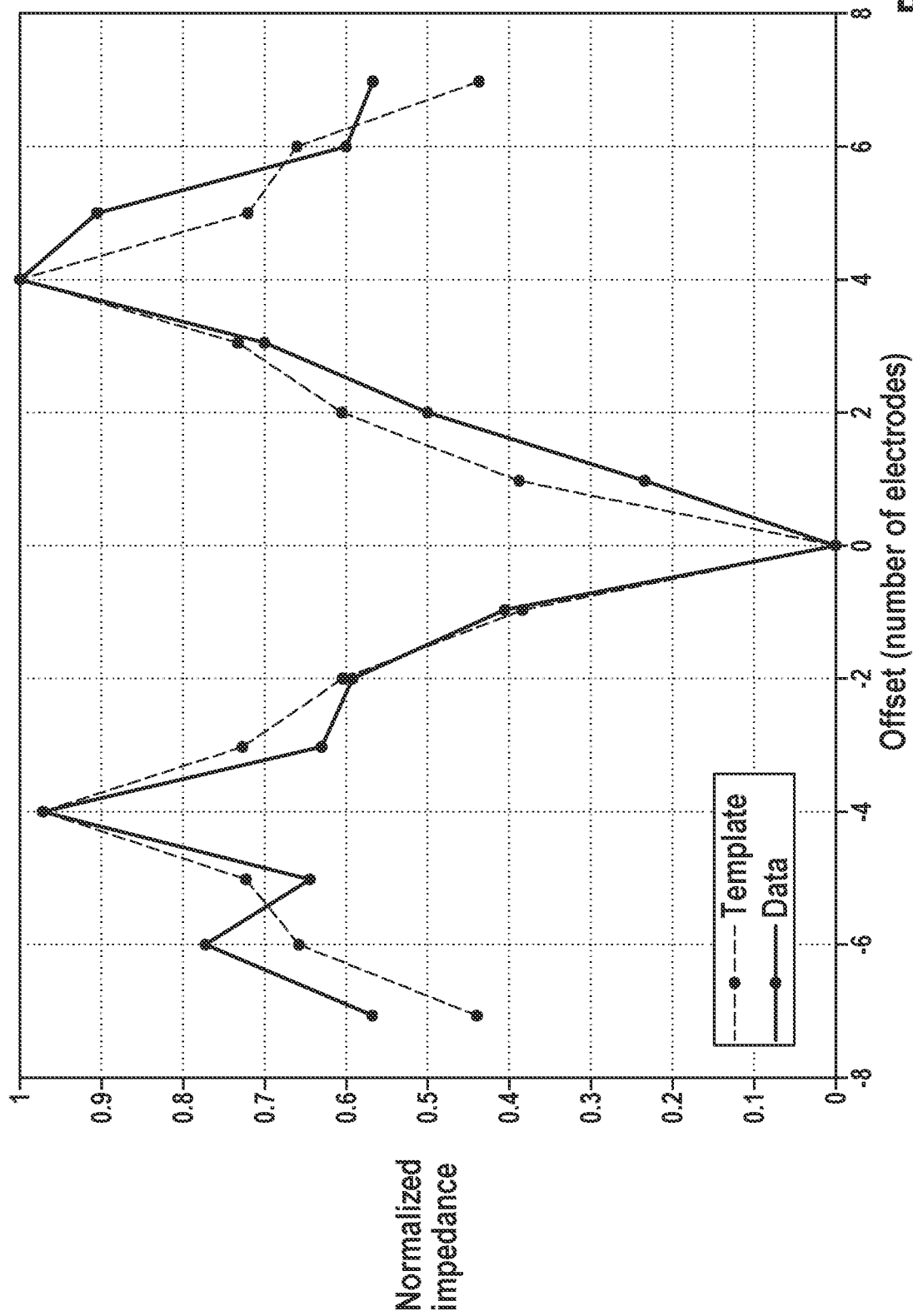
Figure 4C:
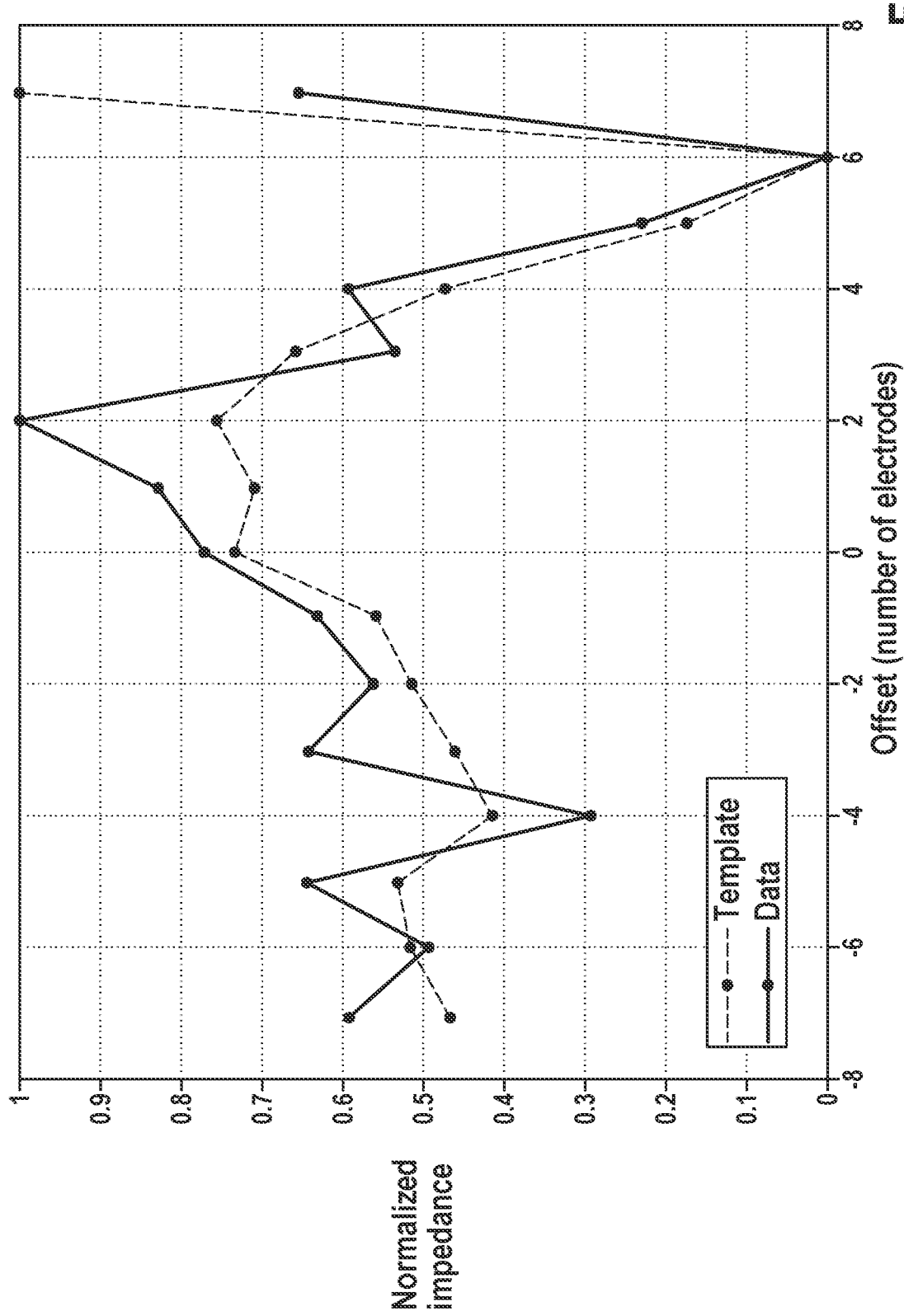
Figure 4D:
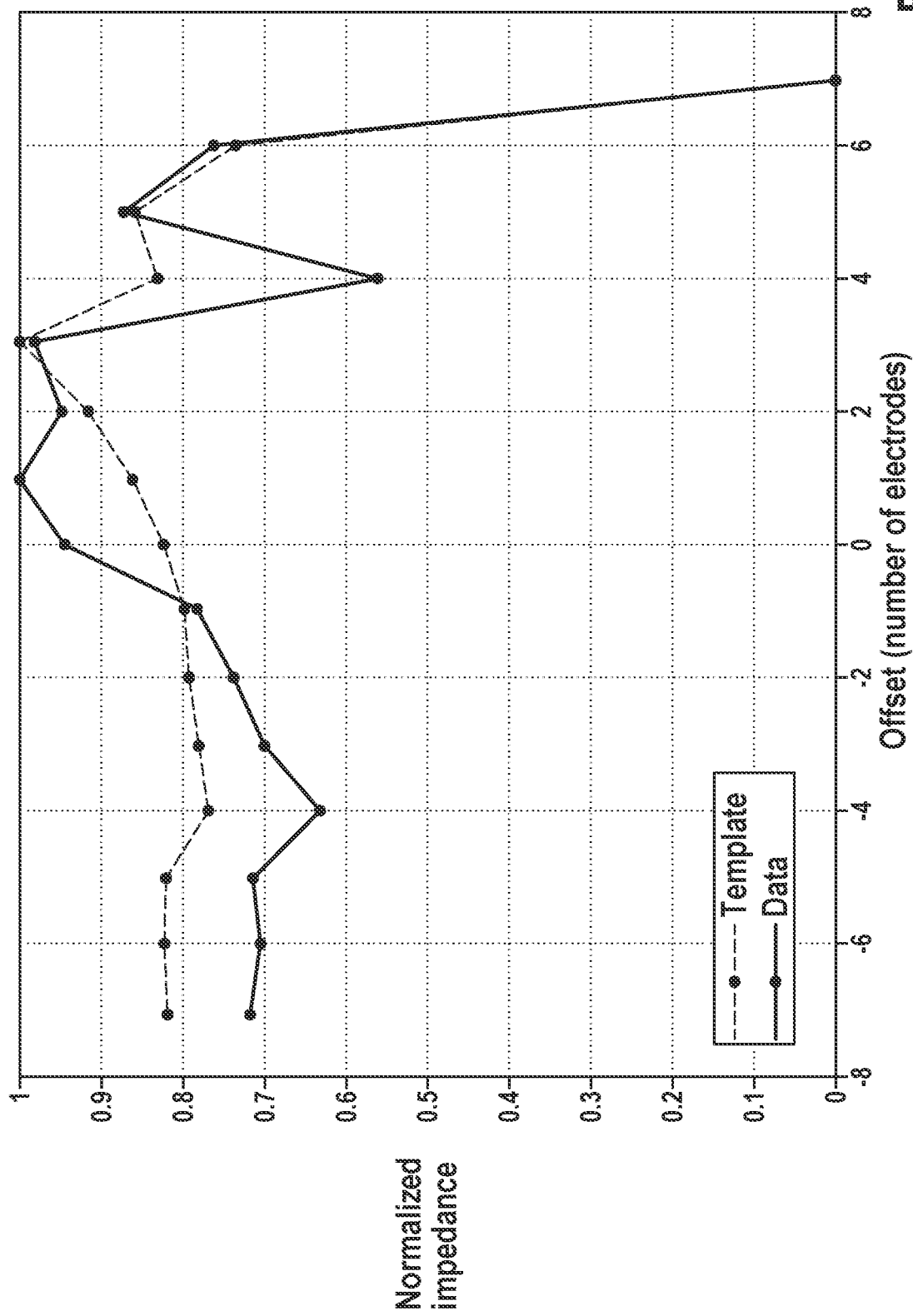
Figure 5A:
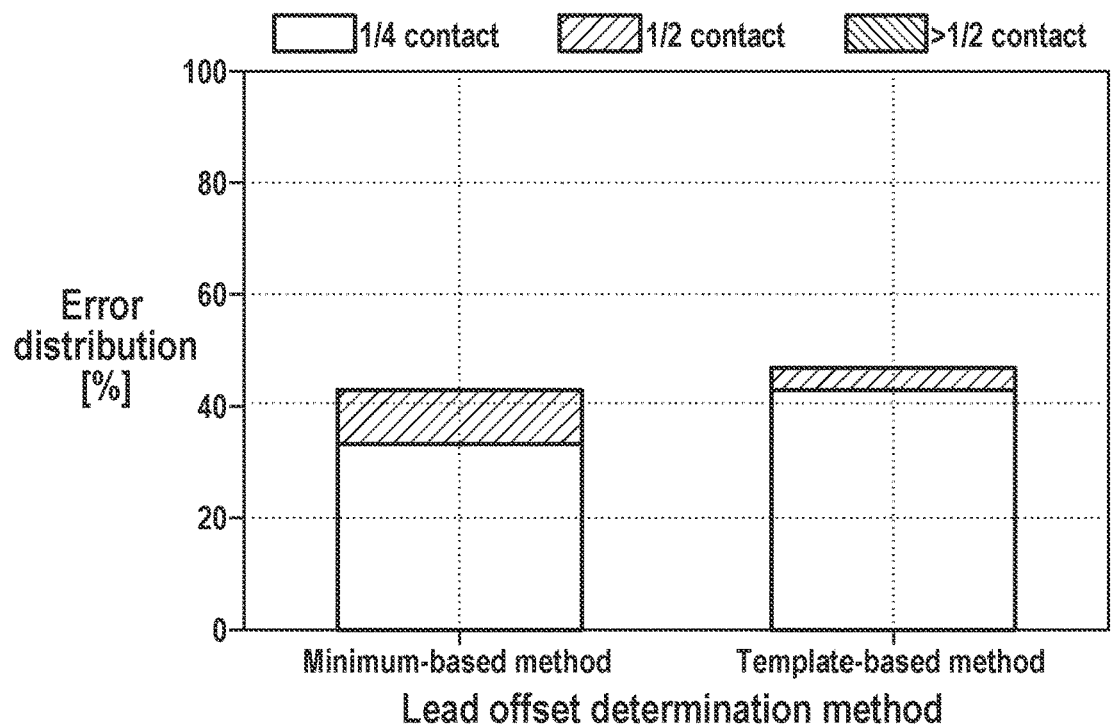
FIGS. 5A and 5B show a distribution of lead offset estimation errors of the method according to the present invention with 5A in-vivo and 5B computationally simulated data. The minimum-based method corresponds to estimations resulting from the use of the method of the minimum impedance value described herein and the template-based method results from the use of the method of the best correlating impedance profile template described herein. The grey shades of the bars show the distribution of errors, from ¼ electrode (contact) to over ½ electrode (contact).
Figure 5B:
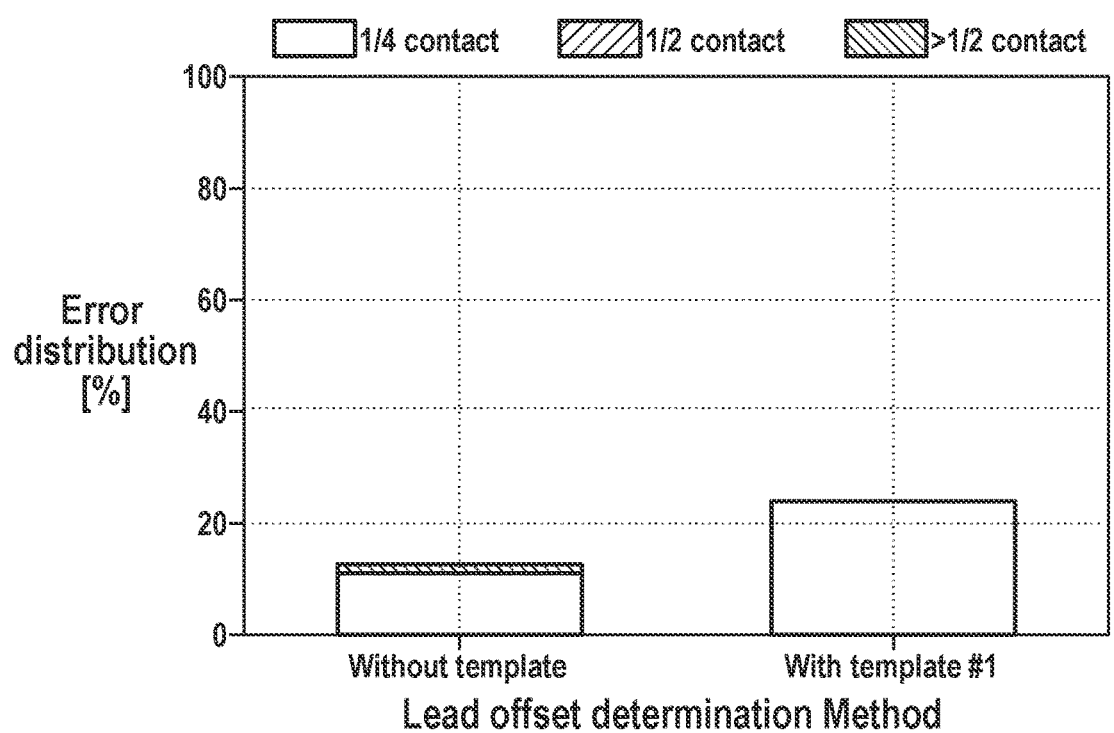

To illustrate the process, four subject impedance data sets superimposed with their respective best correlating template, are shown on FIG. 4. Here, the respective lead offsets of the subject data are FIG. 4A 0.00 electrode, FIG. 4B +0.50 electrode, FIG. 4C +5.50 electrodes and FIG. 4D superior or equal to +7.00 electrodes.

The method according to the present invention presents several technical advantages compared to known solutions. As an example, with a minimum of judiciously selected 32 measurements between two implanted 8-electrode leads, the present invention allows for estimation of the offset that can exist between the leads, with
- a resolution of 0.25 electrodes (one electrode unit is the length of an electrode in longitudinal direction of lead plus the distance between the edges of two adjacent electrodes).
- an accuracy of 0.50 electrodes, which can help for early detection of lead migration and shifts smaller than 1 electrode.
- an allocated memory capacity of the system of only 32 measurements in the present example of 8-electrode leads.
- an independent estimation of the leads relative position without the need of an initial application at implantation to compare to subsequent applications of the method.
- the possibility of remotely performing lead offset determination without requiring hospital facilities or a patient's visit to a hospital, which can help taking appropriate corrective actions, whether it is a reprogramming of the electrostimulation configuration with respect to the estimated lead migration, or a surgical repositioning of the leads.
- the requirement of only an impedance measurement feature (common to many implantable medical devices) to carry out the method according to the present invention.
- At least half the energy consumption compared to techniques that require impedance measurements between all electrodes.
- the relative simplicity to implement the overall method, of which the second (a) and third (c) step can be carried out outside the implanted system to limit further battery consumption.

According to an embodiment, the data generated according to the invention regarding lead offset may be transmitted to an external device and/or data center for further processing, analysis based on automated algorithms or by the user. Moreover, said data and results from data processing and analysis may be provided to the user (e.g. the physician or the nurse).

Furthermore, to illustrate the performance of the present invention with respect to the technical advantages, distributions of estimation errors were calculated using subject data and computationally simulated data. Subject data consisted of 21 impedance data sets from acute implantations of SCS leads, with lead offsets from 0 to +8 electrodes and lead separations from approximatively 1.5 to 5 mm. Simulated data consisted of 2,000 simulations of subject data-based realistic impedance data sets with 0-centered normally distributed lead offsets from −8 to +8 electrodes and uniformly distributed lead separations from 1 to 5 mm. The results are plotted in FIG. 4, which show that there was no estimation error greater than the expected accuracy of ½ electrodes (contacts) both with subject and simulated data.

Figure 6:
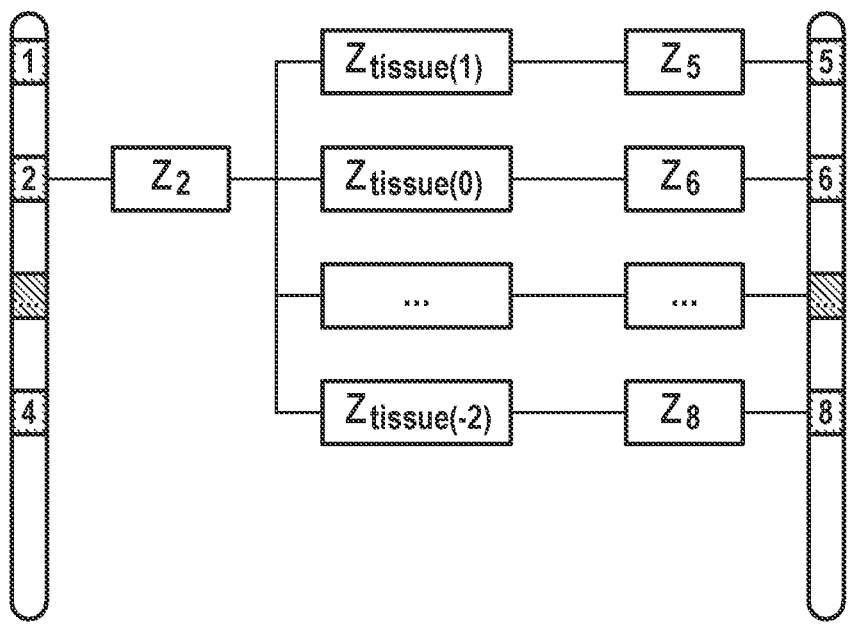
FIG. 6 is a schema illustrating part of the electrical model of impedance measurements.

FIG. 6 shows a schema illustrating part of the electrical model of impedance measurements. $Z_i$ represents the electrode-tissue interface impedance of electrode i, and $Z_{tissue}$ (j) represents the impedance of the tissue portion that separates two electrodes opposed with a longitudinal offset of j contacts.

An embodiment of the invention is based on the concept that inter-electrode impedance measurements can be represented by the electrical model illustrated in FIG. 6. Referring to FIG. 6, for instance, measuring the impedance between electrode 2 and electrode 6 is equivalent to measuring in series the electrode-tissue interface impedance of electrode 2, the bulk impedance of the tissue that separates electrode 2 and 6, followed by the electrode-tissue interface impedance of electrode 6.

If the leads are aligned, the case in the schema of FIG. 6, the portion of tissue separating electrode 2 and 5 is larger than the portion of tissue separating electrode 2 and 6, because of the larger distance between the two electrodes. This larger distance is characterized by an offset of 1 contact between the two contacts, as electrode 5 is just one contact higher than electrode 6 in the longitudinal direction. This pairwise electrode longitudinal offset will be referred to by "contact offset" in the rest of this description, and is explicated for each electrode pair in Table 7. Similarly, in the case of non-aligned leads, the relative position of the leads is expressed in terms of lead offset, in units of contacts. A lead offset of +1 contact would for instance imply that electrode 2 and 5 are aligned.

TABLE 7

Matrix C of contact offsets corresponding to impedance measurements, assuming lead alignment, in units of contacts. Electrodes 1 to 4 of one lead are represented by columns 1 to 4 and electrodes 5 to 8 of the opposed lead by rows 5 to 8

| Electrode # | 1 | 2 | 3 | 4 |
|---|---|---|---|---|
| 5 | 0 | 1 | 2 | 3 |
| 6 | −1 | 0 | 1 | 2 |
| 7 | −2 | −1 | 0 | 1 |
| 8 | −3 | −2 | −1 | 0 |

There are two main steps to carry out the first embodiment, and one to carry out the second embodiment.

Embodiment 1
  Impedance pre-conditioning: identify in those measurements the impedance values of electrode-tissue interfaces and lead offset-related components.
  Lead offset determination: apply the minimum finding method to the pre-conditioned impedance values to find the lead offset.
Embodiment 2: using a contact offset-dependent weigh function.

The two embodiments are described in detail below.

Embodiment 1

A. Impedance Pre-Conditioning

The weight of electrode-tissue interface impedance components in measured inter-electrode impedances is significantly heavier than tissue-related impedance components, although it is the latter that holds information about leads positions. The present invention's first and second feature thus aims at attenuating this factor and extracting the relevant impedance components to allow for lead offset determination in the third invention feature.

The method consists of defining $N=(4*n-1)$ variables, with n the number of electrodes per lead, describing the impedance structure of the dual leads. For 8-electrode leads, that would be 31 variables. For 4-electrode leads, which are used for simplification in this embodiment, that number would be 15. Those variables break down as follows: 8 variables represent the electrode-tissue interface impedance $Z_n$ of each electrode n, and 1 variable $Z_{tissue}$ represents the impedance of the tissue between two opposite electrodes. The tissue impedance between two electrodes that are not facing each other is calculated with a function of the contact difference (the contact offset of the pair (electrode 2, electrode 5) of the example model in FIG. 6 is 1 contact).

Based on this model, a number of equations can be written using the variables described above and all possible inter-lead impedance measurements (64 in case of 8-electrode leads, 16 in case of 4-electrode leads). For instance, the impedance measured between electrode 2 and electrode 5 ($Z_{2,5}$) of the model in FIG. 6 can be described by the following equation:

$$Z_2 + Z_{tissue(1)} + Z_5 = Z_{2,5}$$

Similarly, the equation associated to the impedance measure between electrode 2 and 6 ($Z_{2,6}$) is:

$$Z_2 + Z_{tissue(0)} + Z_6 = Z_{2,6}$$

Note that the number of actual impedance measurements can be lower than the number of possible measurements. In fact, the minimum number of required impedance measurements is equal to the number of defined variables N, that is 31 in case of 8-electrode leads or 15 in case of 4-electrode leads. But the greater the number of impedance measurements, the more performant the method. In the current embodiment of 4-electrode leads, 16 impedance measurements are taken.

Given the 16 impedance measurements available, 16 equations can be written the same way. It gives the following system of equations:

$$\begin{cases} Z_1 + Z_{tissue(0)} + Z_5 = Z_{1,5} \\ Z_1 + Z_{tissue(-1)} + Z_6 = Z_{1,6} \\ \vdots \\ Z_4 + Z_{tissue(0)} + Z_8 = Z_{4,8} \end{cases}$$

This can be written as a matrix product, without changing the meaning of the equations:

$$\begin{pmatrix} 1 & 0 & 0 & 0 & 1 & 0 & 0 & 0 & 0 & 0 & 1 & 0 & 0 & 0 & 0 \\ 1 & 0 & 0 & 0 & 0 & 1 & 0 & 0 & 0 & 1 & 0 & 0 & 0 & 0 & 0 \\ 1 & 0 & 0 & 0 & 0 & 0 & 1 & 0 & 1 & 0 & 0 & 0 & 0 & 0 & 0 \\ 1 & 0 & 0 & 0 & 0 & 0 & 0 & 1 & 1 & 0 & 0 & 0 & 0 & 0 & 0 \\ 0 & 1 & 0 & 0 & 1 & 0 & 0 & 0 & 0 & 0 & 0 & 1 & 0 & 0 & 0 \\ 0 & 1 & 0 & 0 & 0 & 1 & 0 & 0 & 0 & 0 & 1 & 0 & 0 & 0 & 0 \\ 0 & 1 & 0 & 0 & 0 & 0 & 1 & 0 & 0 & 1 & 0 & 0 & 0 & 0 & 0 \\ 0 & 1 & 0 & 0 & 0 & 0 & 0 & 1 & 0 & 1 & 0 & 0 & 0 & 0 & 0 \\ 0 & 0 & 1 & 0 & 1 & 0 & 0 & 0 & 0 & 0 & 0 & 0 & 1 & 0 & 0 \\ 0 & 0 & 1 & 0 & 0 & 1 & 0 & 0 & 0 & 0 & 0 & 1 & 0 & 0 & 0 \\ 0 & 0 & 1 & 0 & 0 & 0 & 1 & 0 & 0 & 0 & 1 & 0 & 0 & 0 & 0 \\ 0 & 0 & 1 & 0 & 0 & 0 & 0 & 1 & 0 & 1 & 0 & 0 & 0 & 0 & 0 \\ 0 & 0 & 0 & 1 & 1 & 0 & 0 & 0 & 0 & 0 & 0 & 0 & 0 & 1 & 0 \\ 0 & 0 & 0 & 1 & 0 & 1 & 0 & 0 & 0 & 0 & 0 & 0 & 1 & 0 & 0 \\ 0 & 0 & 0 & 1 & 0 & 0 & 1 & 0 & 0 & 0 & 0 & 1 & 0 & 0 & 0 \\ 0 & 0 & 0 & 1 & 0 & 0 & 0 & 1 & 0 & 0 & 1 & 0 & 0 & 0 & 0 \end{pmatrix} \begin{pmatrix} Z_1 \\ Z_2 \\ Z_3 \\ Z_4 \\ Z_5 \\ Z_6 \\ Z_7 \\ Z_8 \\ Z_{tissue(-3)} \\ Z_{tissue(-2)} \\ Z_{tissue(-1)} \\ Z_{tissue(0)} \\ Z_{tissue(1)} \\ Z_{tissue(2)} \\ Z_{tissue(3)} \\ 0 \end{pmatrix} = \begin{pmatrix} Z_{1,5} \\ Z_{1,6} \\ Z_{1,7} \\ Z_{1,8} \\ Z_{2,5} \\ Z_{2,6} \\ Z_{2,7} \\ Z_{2,8} \\ Z_{3,5} \\ Z_{3,6} \\ Z_{3,7} \\ Z_{3,8} \\ Z_{4,5} \\ Z_{4,6} \\ Z_{4,7} \\ Z_{4,8} \end{pmatrix}$$

Which can also be written as:

$$AX = B \qquad (1)$$

With:

$$A = \begin{pmatrix} 1 & 0 & 0 & 0 & 1 & 0 & 0 & 0 & 0 & 0 & 1 & 0 & 0 & 0 & 0 \\ 1 & 0 & 0 & 0 & 0 & 1 & 0 & 0 & 0 & 1 & 0 & 0 & 0 & 0 & 0 \\ 1 & 0 & 0 & 0 & 0 & 0 & 1 & 0 & 1 & 0 & 0 & 0 & 0 & 0 & 0 \\ 1 & 0 & 0 & 0 & 0 & 0 & 0 & 1 & 1 & 0 & 0 & 0 & 0 & 0 & 0 \\ 0 & 1 & 0 & 0 & 1 & 0 & 0 & 0 & 0 & 0 & 0 & 1 & 0 & 0 & 0 \\ 0 & 1 & 0 & 0 & 0 & 1 & 0 & 0 & 0 & 0 & 1 & 0 & 0 & 0 & 0 \\ 0 & 1 & 0 & 0 & 0 & 0 & 1 & 0 & 0 & 1 & 0 & 0 & 0 & 0 & 0 \\ 0 & 1 & 0 & 0 & 0 & 0 & 0 & 1 & 0 & 1 & 0 & 0 & 0 & 0 & 0 \\ 0 & 0 & 1 & 0 & 1 & 0 & 0 & 0 & 0 & 0 & 0 & 0 & 1 & 0 & 0 \\ 0 & 0 & 1 & 0 & 0 & 1 & 0 & 0 & 0 & 0 & 0 & 1 & 0 & 0 & 0 \\ 0 & 0 & 1 & 0 & 0 & 0 & 1 & 0 & 0 & 0 & 1 & 0 & 0 & 0 & 0 \\ 0 & 0 & 1 & 0 & 0 & 0 & 0 & 1 & 0 & 1 & 0 & 0 & 0 & 0 & 0 \\ 0 & 0 & 0 & 1 & 1 & 0 & 0 & 0 & 0 & 0 & 0 & 0 & 0 & 1 & 0 \\ 0 & 0 & 0 & 1 & 0 & 1 & 0 & 0 & 0 & 0 & 0 & 0 & 1 & 0 & 0 \\ 0 & 0 & 0 & 1 & 0 & 0 & 1 & 0 & 0 & 0 & 0 & 1 & 0 & 0 & 0 \\ 0 & 0 & 0 & 1 & 0 & 0 & 0 & 1 & 0 & 0 & 1 & 0 & 0 & 0 & 0 \end{pmatrix},$$

$$X = \begin{pmatrix} Z_1 \\ Z_2 \\ Z_3 \\ Z_4 \\ Z_5 \\ Z_6 \\ Z_7 \\ Z_8 \\ Z_{tissue(-3)} \\ Z_{tissue(-2)} \\ Z_{tissue(-1)} \\ Z_{tissue(0)} \\ Z_{tissue(1)} \\ Z_{tissue(2)} \\ Z_{tissue(3)} \\ 0 \end{pmatrix}, B = \begin{pmatrix} Z_{1,5} \\ Z_{1,6} \\ Z_{1,7} \\ Z_{1,8} \\ Z_{2,5} \\ Z_{2,6} \\ Z_{2,7} \\ Z_{2,8} \\ Z_{3,5} \\ Z_{3,6} \\ Z_{3,7} \\ Z_{3,8} \\ Z_{4,5} \\ Z_{4,6} \\ Z_{4,7} \\ Z_{4,8} \end{pmatrix}$$

The unknown variables being contained in X, it can be computed by a simple equation rearrangement:

$$AX = B \Leftrightarrow A^{-1}AX = A^{-1}B \Leftrightarrow X = A^{-1}B \quad (2)$$

Thus, X contains each of the electrode-specific impedances and each of the contact offset-dependent tissue components. The latter contains the information about the actual lead offset.

B. Lead Offset Determination

The method of minimum finding is applied using the pre-conditioned $Z_{tissue}$ terms as follows:

A. Store each $Z_{tissue}$ value in a vector Y in present order of contact offset (i.e from contact offsets −3 to +3) such as $Y = [Z_{tissue(-3)}, \ldots, Z_{tissue(3)}]$.

B. Normalize the data in Y to the interval [0 1].

C. Find the minimum impedance value of vector Y and its corresponding contact offset in Table 7: the latter is the 'integer' offset.

D. Find the impedance values in Y and their corresponding contact offsets in Table 7 that are adjacent to the minimum (if the minimum is located on an extremity of the contact offset range, take the two closest impedance values).

E. Compute the first and second difference of the vector M: [left adjacent value, minimum value, right adjacent value].

F. As shown on FIG. 3A, the comparison of the first and second difference of vector M determines the 'fractional' offset: if the absolute value of the second difference is inferior to ⅓ the maximum of the first difference (i.e. if the circle is in the upper interval in FIG. 3A), then the 'fractional' offset is 0. If it is between ⅓ and ⅔ of the maximum of the first difference (i.e. the circle is in the middle interval in FIG. 3A), then the 'fractional' offset is ¼ contact. If it is between ⅔ and 3/3 (i.e. the circle is in the lower interval in FIG. 3A), then the 'fractional' offset is ½. The sign of the fractional offset is determined by the relative position of the second minimum value among the two data points adjacent to the minimum value: the sign is negative if the second minimum is on the left of the minimum (e.g. circle in FIG. 3A), and positive if it is on its right.

G. The overall contact offset calculated is the sum of the 'integer' and 'fractional' offset.

Embodiment 2

Using a Minimum of (2*n+1) Impedance Measurements (with n Electrodes Per Lead)

Embodiment 2 is the same as embodiment 1 except that all of the $Z_{tissue(-3)}, \ldots, Z_{tissue(+3)}$ terms are reduced to one term $Z_{tissue}$. Each tissue component of the impedance model is represented by a function of the contact offset and $Z_{tissue}$ such as:

$$Z_i + f(x) * Z_{tissue} + Z_j = Z_{i,j}$$

With i the electrode number of the first lead, j the electrode number of the second lead, and x the absolute value of the contact offset (x=1, . . . , 3 with a 4-electrode lead system).

The matrix equations A, X and B from embodiment 1 become:

$$\begin{pmatrix} 1 & 0 & 0 & 0 & 1 & 0 & 0 & 0 & 1 & 0 & 0 & 0 & 0 & 0 & 0 & 0 \\ 1 & 0 & 0 & 0 & 0 & 1 & 0 & 0 & f(1) & 0 & 0 & 0 & 0 & 0 & 0 & 0 \\ 1 & 0 & 0 & 0 & 0 & 0 & 1 & 0 & f(2) & 0 & 0 & 0 & 0 & 0 & 0 & 0 \\ 1 & 0 & 0 & 0 & 0 & 0 & 0 & 1 & f(3) & 0 & 0 & 0 & 0 & 0 & 0 & 0 \\ 0 & 1 & 0 & 0 & 1 & 0 & 0 & 0 & 1 & 0 & 0 & 0 & 0 & 0 & 0 & 0 \\ 0 & 1 & 0 & 0 & 0 & 1 & 0 & 0 & f(1) & 0 & 0 & 0 & 0 & 0 & 0 & 0 \\ 0 & 1 & 0 & 0 & 0 & 0 & 1 & 0 & f(2) & 0 & 0 & 0 & 0 & 0 & 0 & 0 \\ 0 & 1 & 0 & 0 & 0 & 0 & 0 & 1 & f(3) & 0 & 0 & 0 & 0 & 0 & 0 & 0 \\ 0 & 0 & 1 & 0 & 1 & 0 & 0 & 0 & 1 & 0 & 0 & 0 & 0 & 0 & 0 & 0 \\ 0 & 0 & 1 & 0 & 0 & 1 & 0 & 0 & f(1) & 0 & 0 & 0 & 0 & 0 & 0 & 0 \\ 0 & 0 & 1 & 0 & 0 & 0 & 1 & 0 & f(2) & 0 & 0 & 0 & 0 & 0 & 0 & 0 \\ 0 & 0 & 1 & 0 & 0 & 0 & 0 & 1 & f(3) & 0 & 0 & 0 & 0 & 0 & 0 & 0 \\ 0 & 0 & 0 & 1 & 1 & 0 & 0 & 0 & 1 & 0 & 0 & 0 & 0 & 0 & 0 & 0 \\ 0 & 0 & 0 & 1 & 0 & 1 & 0 & 0 & f(1) & 0 & 0 & 0 & 0 & 0 & 0 & 0 \\ 0 & 0 & 0 & 1 & 0 & 0 & 1 & 0 & f(2) & 0 & 0 & 0 & 0 & 0 & 0 & 0 \\ 0 & 0 & 0 & 1 & 0 & 0 & 0 & 1 & f(3) & 0 & 0 & 0 & 0 & 0 & 0 & 0 \end{pmatrix}, X = \begin{pmatrix} Z_1 \\ Z_2 \\ Z_3 \\ Z_4 \\ Z_5 \\ Z_6 \\ Z_7 \\ Z_8 \\ Z_{tissue} \\ 0 \\ 0 \\ 0 \\ 0 \\ 0 \\ 0 \\ 0 \end{pmatrix}, B = \begin{pmatrix} Z_{1,5} \\ Z_{1,6} \\ Z_{1,7} \\ Z_{1,8} \\ Z_{2,5} \\ Z_{2,6} \\ Z_{2,7} \\ Z_{2,8} \\ Z_{3,5} \\ Z_{3,6} \\ Z_{3,7} \\ Z_{3,8} \\ Z_{4,5} \\ Z_{4,6} \\ Z_{4,7} \\ Z_{4,8} \end{pmatrix}$$

Figure 7:
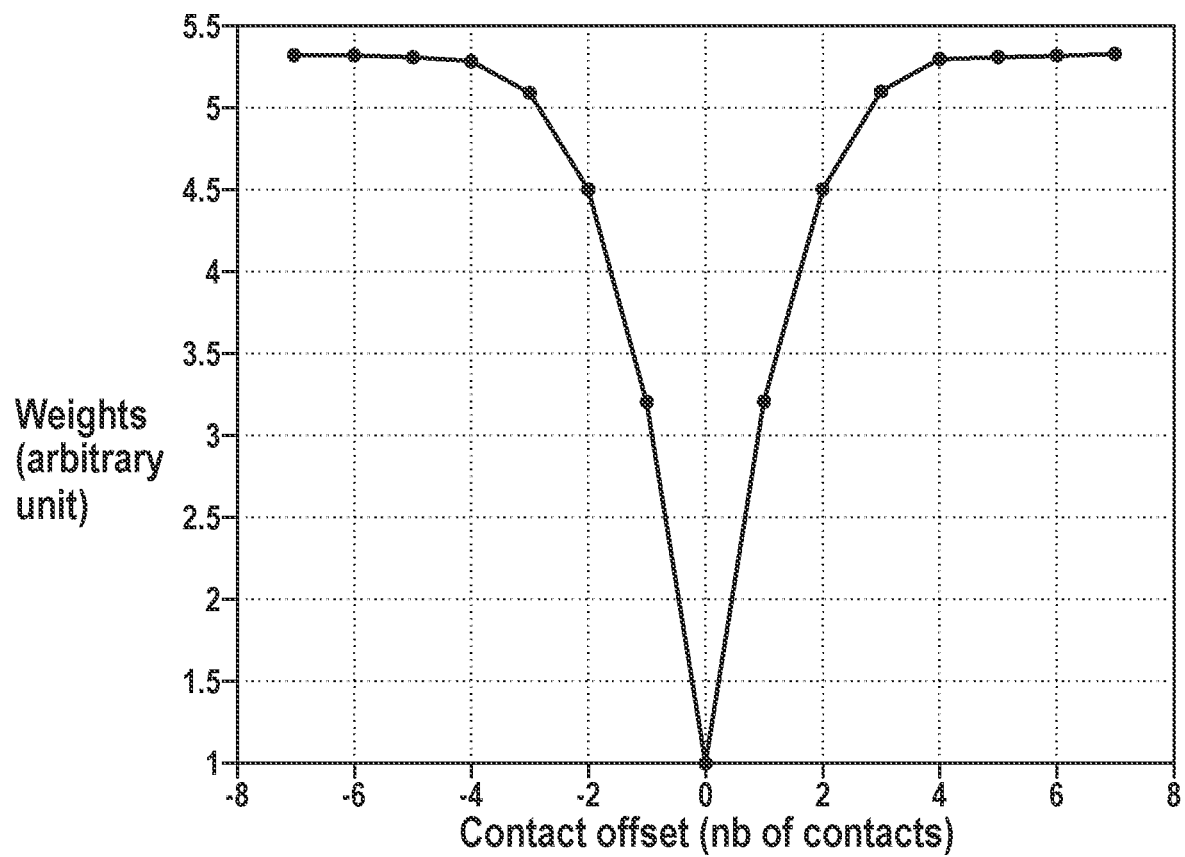
FIG. 7 illustrates the function f used for 8-electrode lead systems, defining tissue impedance (Ztissue) weights versus contact offset.

A crucial element of this method is the definition of the function f. It must represent the impedance variations with the distance that separates two contacts. This function f takes the form of a vector filled with weights for a range of contact offset. It is interpolated over the desired set of contact offsets. See the example for an 8-electrode lead system in The weight function f requires the assumption of a specific lead offset. For instance, FIG. 7 represents the weight function in case of aligned leads (the minimum impedance is at contact offset 0). To determine the lead offset that should be used for the weight function, i.e. to determine the actual lead offset, each contact offset is assumed. For each assumed contact offset, the function f is calculated, vector X is calculated, and X is used again to reconstruct the initial impedance matrix B' and is compared to the real initial matrix B. The assumed contact offset that results in the minimal error between B and B' is the lead offset. The steps are broken down as follows:

a) Assume a contact offset x.
b) Build the corresponding weight function f according to the assumed x.
c) Compute the 9 unknown variables in X using $X=A^{-1}B$ (B is the vector containing the actual impedance measurements)

These 9 unknown variables represent each electrode-specific impedance plus the tissue impedance. Those electrode-specific impedances can be used independently from the rest of the lead offset algorithm to provide information to an end user or unit for other purposes than calculating the lead offset, such as, for example:

A. Provide an end user or unit/system with information about the integrity of each electrode.
B. Provide an end user with an estimated value of electrode impedance that can be used to track impedance change over time or unusually high impedance that can impair therapy efficacy.
C. Provide an end unit/system with electrode-specific impedance in order to calculate the maximum current limit of a given electrode configuration that uses one or multiple electrodes before the therapy is turned on and thus ensure stimulation safety.
D. Reconstruct the initial impedance matrix B' using the 9 computed variables (stored in vector X) and AX=B.
E. Calculate the root mean square error (RMSE) between the original and reconstructed impedance matrices B and B'.
F. Repeat 1. through 5. for each contact offset assumption x (from −3 contact to 3 contacts with a step of 0.5).
G. Define the actual lead offset as the lead offset assumption that resulted in the minimum RMSE.

Moreover, multi-electrode leads implanted in the human body usually require positioning in a medium close to the therapy target to deliver electrical stimulation. In many neurostimulation applications, the stimulation current must cross both a resistive tissue portion such as fatty tissue and a conductive fluid such as blood or the cerebrospinal fluid in order to reach target excitable cells, for example the spinal cord. The position of the electrodes with respect to one of the portions is an important factor of the efficiency and success of these therapies, but there is usually little knowledge of that relative position following implant. Having access to that information can provide new insights into therapy's outcomes and could shed light on the importance of a neglected parameter of electrical stimulation therapies, and particularly in neuromodulation.

According to an embodiment of the present invention, a method and device for estimating the proximity of a multi-electrode lead to a local conductivity discontinuity are disclosed. Currently, no solution is known for such subject. In case of large lead-to-fluid distance (e.g. SCS lead-to-CSF distance), not having any sense of the distance between the lead and the fluid medium prevents from taking corrective action to reduce this distance, which can result in nonoptimal therapy or therapy failure.

The objective of this invention is to provide information on the distance between a lead implanted in a medium M1 (e.g. fatty tissue) and a nearby medium M2 (e.g. cerebrospinal fluid, blood), where M1 has a significantly different conductivity than M2. Benefits from that information include ability to inform therapy adjustment, correction of the implant position, optimization of therapy programming, and/or new insights into therapy's parameters and factors of success.

Using the known conductivity difference between local electrode implantation tissue and adjacent fluid media, the method consists of taking multiple impedance measurements between electrodes with close spacing and electrodes with distant spacing. The difference between these measurements is used to estimate the proximity between the lead and a nearby medium.

Figure 8:
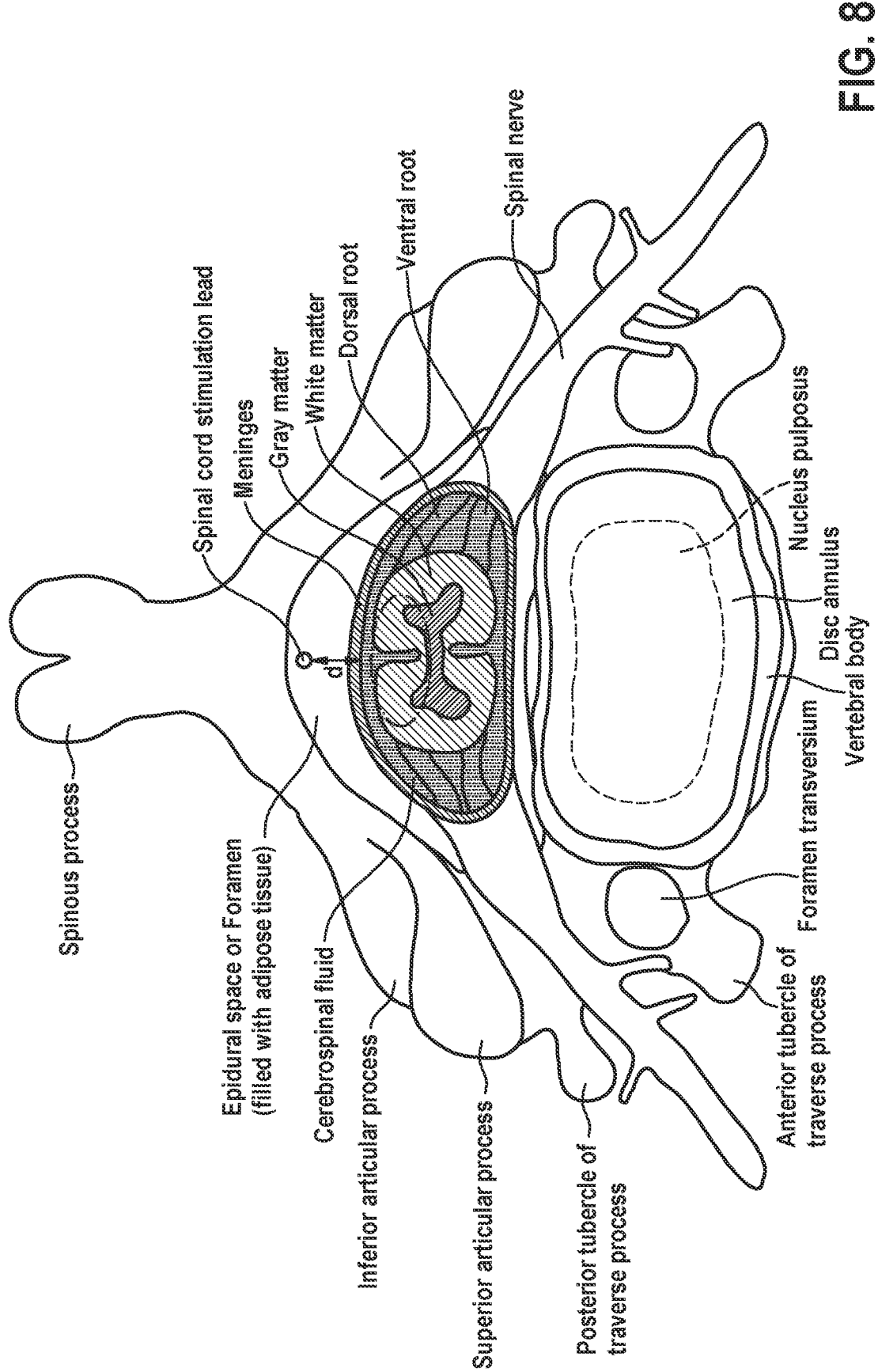
FIG. 8 shows a spinal cord cross section showing the main structures.

FIG. 8 shows a schema of a spinal cord cross section showing the main structures. The red arrow with an adjacent 'd' represents the distance between an implanted SCS lead and the cerebrospinal fluid (CSF). The blue dotted circle depicts the target of electrical stimulation in spinal cord stimulation therapies.

The position of electrodes implanted in the human body is usually assessed by x-ray imaging, and not all tissue structures are visible in those images (e.g. the epidural fat and the cerebrospinal fluid (CSF) in the spinal cord are usually not discernable on X-Ray images). As a result, exact position of electrodes with respect to relevant tissue structures is usually imprecise. For example, the distance between a spinal cord stimulation (SCS) lead implanted in the epidural fat and the CSF (see FIG. 8) is usually not known despite that it plays a role in the therapy efficiency.

An SCS lead is ideally placed the closest to the CSF so that electrical current can flow through the CSF into the spinal cord (see FIG. 8). But in reality, imaging techniques during lead implant give little information about the distance of the lead from the CSF and the final lead location in the epidural fat can be at various distances from the CSF. This concept can be generalized to any therapy involving a group of electrodes on a lead implanted in a resistive tissue that involves delivering electrical current to or through a conductive medium.

Electrodes are usually implanted in tissues (e.g. adipose tissue) that have an electrical conductivity significantly lower than human body fluids (e.g. CSF, blood). Impedance measurements between two electrodes are driven by high resistance components. This means that, if there is a component with a high impedance followed by a component with high conductivity between two electrodes, the size of that conductive component will have little effect on the overall impedance between the two electrodes, because most of the impedance is due to the highly resistant component. In the example of SCS, the epidural fat between the electrodes and the CSF drives the overall impedance between two electrodes. The extent to which it drives this impedance depends on the actual size of the epidural fat portion, i.e. the distance between the electrodes and the CSF. This variation can be captured by comparing the impedance between two adjacent electrodes and two distant electrodes on the same implanted device.

Embodiment 3

In spinal cord stimulation (SCS), a multi-electrode lead composed of 8 cylindrical contacts separated by insulating material is implanted in the epidural fat. It is connected to a pulse generator implanted in a distal location such as the lower back. It is programmed to deliver electrical current through the electrodes to stimulate neurons in the spinal cord. The spinal cord where the target neurons are located is composed of white and grey matter. It is surrounded by the circulating CSF contained in the subarachnoid space. That subarachnoid space is wrapped around by the dura mater, a thick tissue layer that separates the subdural space from the surrounding epidural fat where the leads are implanted. The current pathway from electrodes to spinal cord neurons thus crosses epidural fat tissue, the dura mater and the CSF. The epidural fat and dura mater have significantly higher resistivity than CSF. The disclosed method can be applied in this case to give information about the proximity of the lead to the CSF.

A necessary step to carry out the disclosed method is to remove or attenuate the electrode-tissue interface impedance by pre-conditioning the impedance measurements. To that purpose, a method similar to the method disclosed in the filed patent application 17.109P-US can be applied:

A. Impedance is measured between all possible pairs of electrodes on the lead (eXeY with X=1, . . . , 8 and Y=1, . . . , 8 with X #Y in the case of an 8-electrode lead)

B. Impedance average ZeX (X=1, . . . , 8) is calculated for each electrode X across all impedance measurement involving electrode X C. Impedance average ZeX is removed from each impedance measurement involving electrode X.

Figure 10:
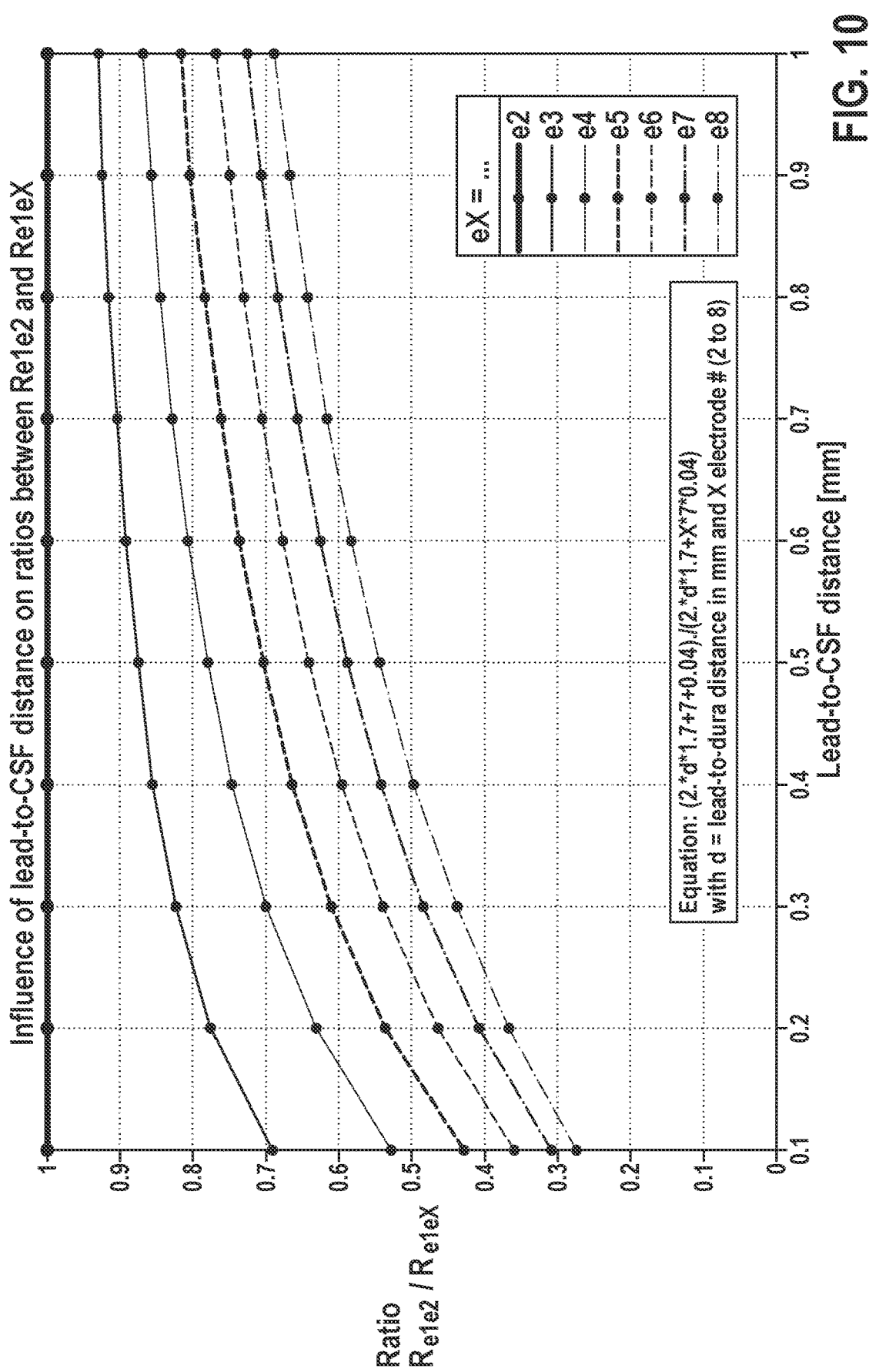
FIG. 10 illustrates the estimation of the variation of ratio R according to lead-to-CSF distance using mathematical equations based on the model illustrated in FIG. 9 and realistic spinal cord dimensions and conductivities.

The method consists in calculating the ratio of the impedance between two adjacent electrodes (e1,e2) to the impedance between two most distant electrodes (e1,e8) on the same lead, with one common electrode (e1) between the two electrode pairs (see Figure). This ratio varies significantly according to the distance between the lead and the dura based on the theory described in section 3.1. Note that the third electrode (e8 in this embodiment) does not necessarily have to be the furthest away from e1, but the further the third electrode, the more performant the method. The variation of the ratio with the lead-to-dura CSF has been mathematically modeled with realistic spinal cord dimensions and conductivities and is represented in FIG. 10.

The method comprises the following steps:
Measure the impedance Ze1e2 between electrode e1 and an adjacent electrode e2.
Measure the impedance Ze1e8 between e1 and e8, the furthest electrode from e1.
Calculate the ratio R=Ze1e2/Ze1e3.
Deduce from R the distance between the lead and the CSF:
If R is small (R<0.5), then the lead is close to the CSF.
If R is large (R>0.5), then the lead is far from the CSF.

Figure 9:
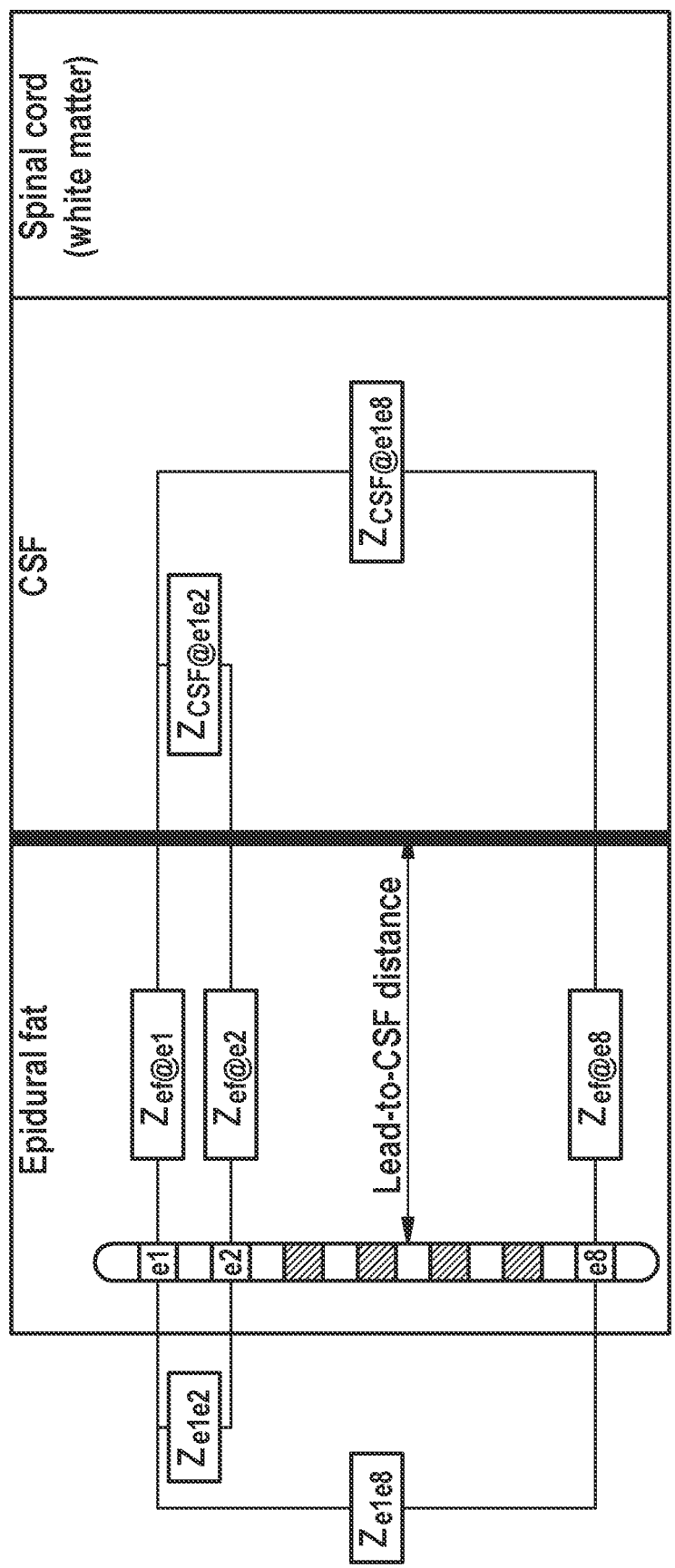
FIG. 9 shows a schematic representation of the coronal plan of the spinal cord.

FIG. 9 shows a schematic representation of the coronal plan of the spinal cord. Dimensions are not drawn to scale. The impedance Ze1e2 between electrode e1 and electrode e2 can be represented by a simple sequence of three resistive components such that Ze1e2=Zef@e1+ZCSF@e1 e2+Zef@e2. Likewise, Ze1e8=Zef@e1+ZCSF@e1 e8+Zef@e8. Zef@e1 and Zef@e2 represent the impedance of the epidural fat tissue between electrode 1 and the CSF, and electrode 2 and the CSF, respectively. ZCSF@e1 e2 represents the impedance of the CSF portion between electrode 1 and electrode 2.

In this specific embodiment, the center-to-center distance between two electrodes is 7 mm. The lead-CSF distance is variable but is in the range of hundreds of micrometers to a couple of millimeters. Because of that difference in distance, during impedance measurement between two electrodes of a lead, the current's least resistive path is to flow into the CSF, travel in the CSF along the spinal cord and then back into the epidural space to reach the second electrode of the measurement pair, as depicted in Figure. Note that this is generalizable to any lead with inter-electrode separations significantly larger than lead-to-dura distances.

FIG. 10 shows an estimation of the variation of ratio R according to lead-to-CSF distance using mathematical equations based on the model illustrated in FIG. 9 and realistic spinal cord dimensions and conductivities.

Embodiment 4

Embodiment 4 is similar to embodiment 3 and uses the same lead dimensions, except that the calculation steps are slightly different: a series of ratios between impedance measurements of more than two pairs of electrodes are calculated. It is the difference between these ratios that depends on the lead proximity to the CSF: the total sum of the calculated differences greatly increases with the proximity of the lead to the CSF, and vice-versa.

The method comprises the following steps:
Measure the impedance Ze1eX between electrode e1 and electrode X, with X=2, . . . , up to the maximum number of electrodes on the lead (in this embodiment X=2, . . . , 8).
Calculate the ratios RX=Ze1e2/Ze1eX, with X=3, . . . , 8.
Calculate the differences DY (Y=1, . . . , 5) between consecutive ratios R4−R3, R5−R4, . . . , R8−R7.
Calculate the absolute value of the sum S of all DY (Y=1, . . . , 5)
Deduce from S the distance between the lead and the CSF:
If S is small (R<0.5), then the lead is far from the CSF.
If S is large (R>0.5), then the lead is close to the CSF.

Figure 11:
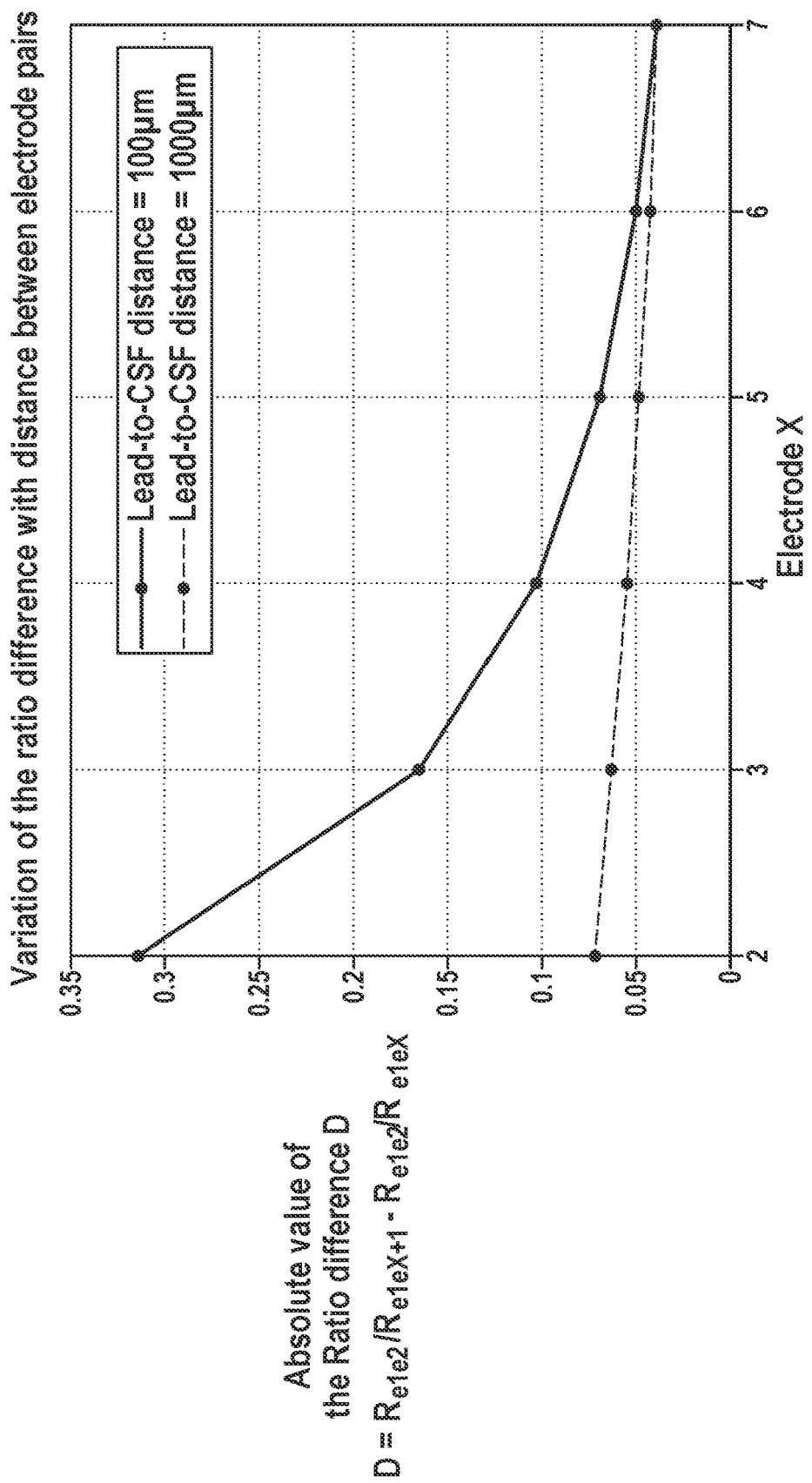
FIG. 11 illustrates the estimation of the variation of ratio differences D according to electrode pair distance, using mathematical equations based on the model illustrated in FIG. 9 and realistic spinal cord dimensions and conductivities.

This embodiment stems from the concept that when the lead is close to the CSF, the overall impedance will be driven by the CSF impedance component and will therefore increase in a logarithmic fashion with electrode distance, as illustrated in FIG. 11. On the opposite, if the lead is far away from the CSF, the overall impedance is driven by the epidural fat and the distance between the electrodes increases the impedance in a constant manner. This translates in a linear increase of impedance with electrode distance, as shown on FIG. 11.

Thus, the difference between two consecutive ratios is different depending on the lead-to-CSF distance: when the lead is close to the CSF, the ratio difference is large between close electrodes, and decreases with electrode distance, whereas the ratio difference remains small when the lead is far away from the CSF. This can be captured by calculating the absolute value of the sum S of all the ratio differences: a small sum reflects little impedance variation across electrode pairs despite the electrode distance, whereas a large sum suggests high impedance variation across electrode pairs, which means higher sensitivity to the distance between electrodes of a pair.

FIG. 11 shows an estimation of the variation of ratio differences D according to electrode pair distance, using mathematical equations based on the model illustrated in FIG. 9 and realistic spinal cord dimensions and conductivities. When lead-to-CSF distance is 100 micrometers, the area under the curve (i.e. the value of sum S) is significantly larger than when the lead-to-CSF distance is 1000 micrometers.

According to an embodiment, to estimate the proximity of a lead implanted in a medium M1 to a medium M2, the method requires the lead to have a minimum of 3 separate electrodes of varying length and spacing.

The medium M1 in which the lead is implanted must have a conductivity significantly different from the medium M2. The lead, or a system connected to the lead, can perform impedance measurements between at least two pairs of electrodes of the same lead.

The method requires a system that can process (live or offline) basic calculus operations (sum, difference, division to calculate ratios) and comparison (superior/inferior) and output the information about lead proximity to the medium M2.

Embodiments of the invention provide a mean to estimate the lead-to-fluid distance in implanted devices, which has currently no known solutions. It is a rapid (few seconds), easy to implement method that requires little computation time and energy to run, and can be applied to any implanted device that possess multiple electrodes at different distances and that can run impedance measurements, which is a common feature already implemented in implanted devices.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A method for estimating an offset between a first group and a second group of contacts with respect to a longitudinal direction or a position of a first group of contacts or a second group of contacts with respect to a longitudinal direction, wherein each group of contacts comprises a plurality of electrodes arranged along a surface of a body of a lead, the method comprising the steps of:
   (a) selecting a number N of electrode pairs, each electrode pair including an electrode of the first group of contacts and an electrode of the second group of contacts, and measuring impedances between the electrodes of each selected electrode pair;
   (b) pre-conditioning the impedances thus measured for attenuating unwanted noise and to generate pre-conditioned impedances; and
   (c) determining the lead offset or position using the pre-conditioned impedances.

2. The method according to claim 1, wherein the step of pre-conditioning the measured impedances for attenuating unwanted noise to generate pre-conditioned impedances comprises:
   calculating for each electrode of the second group an average impedance from the measured impedances of the electrode pairs including the respective electrode and subtracting the average impedance from the measured impedances of the electrode pairs that include the respective electrode to obtain processed impedances; and
   calculating for each electrode of the first group an average processed impedance from the processed impedances of the electrode pairs including the respective electrode of the first lead and subtracting the average processed impedance from the processed measured impedances of the electrode pairs that include the respective electrode of the first lead to obtain the pre-conditioned impedances.

3. The method according to claim 1, wherein the number N of selected electrode pairs is equal to or smaller than a number of all possible electrode pairs.

4. The method according to claim 1, wherein each of the electrodes of the first group and the second group, respectively, is included in the number of selected electrode pairs.

5. The method according to claim 1, wherein one or more of the following are true:
   each of the leads comprises 8 electrodes
   the number N of selected electrode pairs equals 32;
   each of the electrodes of the first and the second lead is included in four electrode pairs;
   the selected electrode pairs are selected such that all electrode offsets between an electrode of the first lead and an electrode of the second lead are present in a range from −7 to 7 electrodes, the range depending on a total number of electrodes and number of electrode pairs respectively.

6. The method according to claim 1, wherein the method is configured to estimate the lead offset with an accuracy or resolution of less than one electrode, defined by:
   one width of an electrode in the longitudinal direction plus the longitudinal distance between the edges of two neighboring electrodes; or
   a distance from a center of a width of an electrode to a center of a width of a neighboring electrode.

7. The method according to claim 1, wherein the step of determining the lead offset using the pre-conditioned impedances comprises calculating for each electrode offset between an electrode of the first lead and an electrode of the second lead an average impedance value corresponding to an average of the pre-conditioned impedance values for the respective electrode offset.

8. The method according to claim 7, wherein the step of determining the lead offset further comprises finding a minimum impedance value among the average pre-conditioned impedance values, wherein the electrode offset corresponding to the minimum impedance value is an integer offset, and wherein the lead offset to be determined is a sum of the integer offset and a fractional offset.

9. The method according to claim 8, which comprises determining the fractional offset by extracting two impedance values from average pre-conditioned impedance values, wherein the two impedance values correspond to two electrode offsets neighboring the electrode offset associated with the minimum impedance value.

10. The method according to claim 1, wherein the step of determining the lead offset using the pre-conditioned impedances comprises:
   calculating for each electrode offset between an electrode of the first lead and an electrode of the second lead an average impedance value corresponding to an average of the pre-conditioned impedance values for the respective electrode offset; and
   forming a pre-conditioned impedance profile, wherein the pre-conditioned impedance profile comprises the averages of the pre-conditioned impedance values versus the electrode offsets, and wherein a plurality of template profiles is provided, wherein each template profile corresponds to a detectable lead offset, and includes impedance values versus lead offset values; and
   calculating correlation coefficients between the pre-conditioned impedance profile and all of the template profiles, wherein the lead offset is estimated to be the lead offset of the template profile corresponding to a greatest correlation coefficient.

11. A system for estimating a positional electrode offset between a first group of electrodes and a second group of electrodes, the system comprising:
- a measuring unit for measuring Impedances between the electrodes of a number N of selected electrode pairs;
- an analyzing unit configured to pre-condition the measured impedances; and
- a calculation unit configured to calculate the electrode offset between the group of electrodes using the pre-conditioned impedances.

12. The system according to claim 11, wherein the calculation unit is configured to calculate the electrode offset between groups with an accuracy or resolution of less than one distance from a center of one electrode to a center of at least one second electrode.

13. A system for estimating a lead offset between a first lead and a second lead with respect to a longitudinal direction, along which the respective lead extends, the system comprising:
- a first lead and a second lead, each lead including a plurality of electrodes arranged along a surface of a body of the respective lead;
- a measuring unit for measuring impedances between the electrodes of a number of selected electrode pairs, each electrode pair including an electrode of the first lead and an electrode of the second lead;
- an analyzing unit configured to pre-condition the impedances measured by said measuring unit for attenuating unwanted noise and to generate pre-conditioned impedances, said analyzing unit being configured to:
  - calculate for each electrode of the second lead an average impedance from the measured impedances of the electrode pairs containing the electrode and subtracting the average impedance from the measured impedances of the electrode pairs containing the electrode to obtain processed impedances; and
  - calculate for each electrode of the first lead an average processed impedance from said processed impedances of the electrode pairs containing the electrode of the first lead and subtracting the average processed impedance from the processed measured impedances of the electrode pairs containing the electrode of the first lead to obtain said pre-conditioned impedances; and
  - determine the lead offset using the pre-conditioned impedances.

* * * * *